US012582293B2

(12) United States Patent
Horie et al.

(10) Patent No.: US 12,582,293 B2
(45) Date of Patent: Mar. 24, 2026

(54) INSERTION INSTRUMENT AND ENDOSCOPE SYSTEM

(71) Applicant: OLYMPUS MEDICAL SYSTEMS CORP., Tokyo (JP)

(72) Inventors: Satoshi Horie, Kokubunji (JP); Nagahide Sakai, Kodaira (JP)

(73) Assignee: Olympus Medical Systems Corp., Tokyo (JP)

( * ) Notice: Subject to any disclaimer, the term of this patent is extended or adjusted under 35 U.S.C. 154(b) by 468 days.

(21) Appl. No.: 18/210,085

(22) Filed: Jun. 15, 2023

(65) Prior Publication Data

US 2023/0414071 A1 Dec. 28, 2023

Related U.S. Application Data

(60) Provisional application No. 63/355,186, filed on Jun. 24, 2022.

(51) Int. Cl.
*A61B 1/00* (2006.01)
*A61B 1/05* (2006.01)

(52) U.S. Cl.
CPC ...... *A61B 1/00096* (2013.01); *A61B 1/00094* (2013.01); *A61B 1/05* (2013.01); *A61B 1/0011* (2013.01)

(58) Field of Classification Search
CPC ............ A61B 1/00091; A61B 1/00094; A61B 1/00096; A61B 1/015; A61B 1/05; A61B 1/051; A61B 1/053; A61B 1/126
See application file for complete search history.

(56) References Cited

U.S. PATENT DOCUMENTS

| | | | | |
|---|---|---|---|---|
| 5,386,817 A | * | 2/1995 | Jones | A61B 1/00135 |
| | | | | 600/125 |
| 6,142,932 A | * | 11/2000 | Morizumi | A61B 1/00193 |
| | | | | 600/176 |
| 6,409,657 B1 | * | 6/2002 | Kawano | A61B 1/125 |
| | | | | 600/157 |
| 8,491,467 B2 | * | 7/2013 | Miyamoto | A61B 1/12 |
| | | | | 600/129 |
| 2011/0082336 A1 | * | 4/2011 | Ito | A61B 1/126 |
| | | | | 600/129 |

(Continued)

FOREIGN PATENT DOCUMENTS

| | | |
|---|---|---|
| JP | 2006-014925 A | 1/2006 |
| JP | 2010-046300 A | 3/2010 |

(Continued)

*Primary Examiner* — Michael J Carey
*Assistant Examiner* — Stephen Floyd London
(74) *Attorney, Agent, or Firm* — Morgan, Lewis & Bockius LLP

(57) ABSTRACT

An insertion instrument comprises an insertion section including a distal end portion, a bending portion, and a flexible tube portion. The distal end portion includes an opening, an objective lens, a first conduit, and a second conduit connected to the first conduit, the second conduit extending in a direction other than the longitudinal direction, the second conduit located distally relative to the first conduit. A space between a side surface of the objective lens and a side surface of the opening in the distal end surface defines a third conduit, the third conduit connected to the second conduit.

20 Claims, 22 Drawing Sheets

(56)                    References Cited

U.S. PATENT DOCUMENTS

| | | | | |
|---|---|---|---|---|
| 2014/0371763 | A1* | 12/2014 | Poll ........................ | A61B 34/30 |
| | | | | 606/130 |
| 2015/0112132 | A1* | 4/2015 | Nieman ............. | A61B 1/00142 |
| | | | | 600/122 |
| 2015/0182108 | A1* | 7/2015 | Fukuda .............. | A61B 1/00091 |
| | | | | 600/157 |
| 2015/0374212 | A1* | 12/2015 | Drach ................. | A61M 5/3137 |
| | | | | 600/123 |
| 2017/0296038 | A1* | 10/2017 | Gordon ............. | A61B 1/00091 |
| 2018/0000320 | A1* | 1/2018 | Nieman ............... | A61B 1/0008 |
| 2018/0160886 | A1* | 6/2018 | Govani ............. | A61B 1/00137 |
| 2019/0110675 | A1* | 4/2019 | Faria ................. | G02B 23/2484 |
| 2020/0008659 | A1* | 1/2020 | Viebach ............. | A61B 1/00174 |
| 2020/0060519 | A1* | 2/2020 | Wake .................... | A61B 1/126 |
| 2021/0030261 | A1* | 2/2021 | Kress ................... | A61B 1/0125 |
| 2021/0076924 | A1* | 3/2021 | Yamaya ............. | A61B 1/00101 |
| 2021/0085158 | A1 | 3/2021 | Ikuma et al. | |
| 2021/0228064 | A1* | 7/2021 | Sorensen ............... | A61B 1/126 |
| 2023/0248434 | A1* | 8/2023 | Altshuler ........... | A61B 1/00091 |
| | | | | 600/108 |

FOREIGN PATENT DOCUMENTS

| | | | |
|---|---|---|---|
| JP | 4441070 | B2 | 3/2010 |
| JP | 4745725 | B2 | 8/2011 |
| JP | 4953748 | B2 | 6/2012 |
| WO | 2019/176171 | A1 | 9/2019 |

\* cited by examiner

INSERTION INSTRUMENT AND ENDOSCOPE SYSTEM

CROSS REFERENCE TO RELATED APPLICATION

This application claims benefit of Provisional Application No. 63/355,186 filed in United States of America on Jun. 24, 2022, the entire contents of which are incorporated herein by this reference.

FIELD OF DISCLOSURE

The present disclosure relates to an insertion instrument including a flow path capable of supplying fluid into a subject.

BACKGROUND

An insertion instrument such as an endoscope has been widely used in a medical field. The insertion instrument includes an elongated insertion portion insertable into a subject. A user is capable of performing observation of an inside of the subject, treatment for a lesioned part in the subject, and the like by inserting the insertion portion into the subject.

In general, an insertion instrument such as an endoscope includes a conduit for guiding fluid such as liquid to a distal end side of an insertion portion. The fluid guided by the conduit is jetted from an opening such as a nozzle provided in a distal end constituting portion (see, for example, Japanese Patent Application Laid-Open Publication No. 2010-46300). Consequently, the fluid guided to the distal end constituting portion by the conduit is used for, for example, cleaning of an observation window.

In an insertion instrument such as a ureteropelvic endoscope, fluid guided by a conduit is perfused into a subject. The fluid retained in the subject by the perfusion expands an inside of the subject. Consequently, a visual field in the subject is extended. A part of the fluid discharged to an outside of the subject by the perfusion is capable of conveying fractured calculi and the like.

SUMMARY

An insertion instrument according to an aspect of the present disclosure includes: an insertion section including a distal end portion, a bending portion, and a flexible tube portion. In a longitudinal direction of the insertion section, the bending portion is between the distal end portion and the flexible tube portion. The flexible tube portion is at a proximal end of the insertion section and the distal end portion is at a distal end of the insertion section. The distal end portion includes: an opening in a distal end surface of the distal end portion, an objective lens located in the opening, the objective lens having a field of view, a first conduit extending in the longitudinal direction, a second conduit connected to the first conduit, the second conduit extending in a direction other than the longitudinal direction, the second conduit located distally relative to the first conduit. A space between a side surface of the objective lens and a side surface of the opening in the distal end surface defines a third conduit, the third conduit connected to the second conduit. The first conduit, the second conduit and the third conduit form a flow path including a first flow path section located in the first conduit, a second flow path section section located in the second conduit, and a third flow path section located in the third conduit.

DETAILED DESCRIPTION

In general, fluid perfused into a subject may be discharged from an opening of a distal end constituting member at a degree of gentle flow velocity for not moving an observation target object and a treatment target object.

Therefore, in a procedure involving the perfusion of the fluid, for example, when cleaning of an observation window, the fluid may not to be powerfully jetted into the subject. On the other hand, in recent years, in an insertion instrument such as an endoscope, a conduit tends to be reduced in diameter according to a reduction in diameter of an insertion portion. In such an insertion instrument, in order to secure a flow rate of the fluid, flow velocity of fluid flowing in the conduit may be increased. When the fluid increased in the flow velocity directly perfuses into the subject, it is likely that a flow of the fluid due to the perfusion is disturbed and the observation target object and the treatment target object greatly move.

According to an embodiment explained below, it is possible to provide an insertion instrument that can secure a visual field of an observation window without disturbing a flow of fluid due to perfusion.

Figure 1:
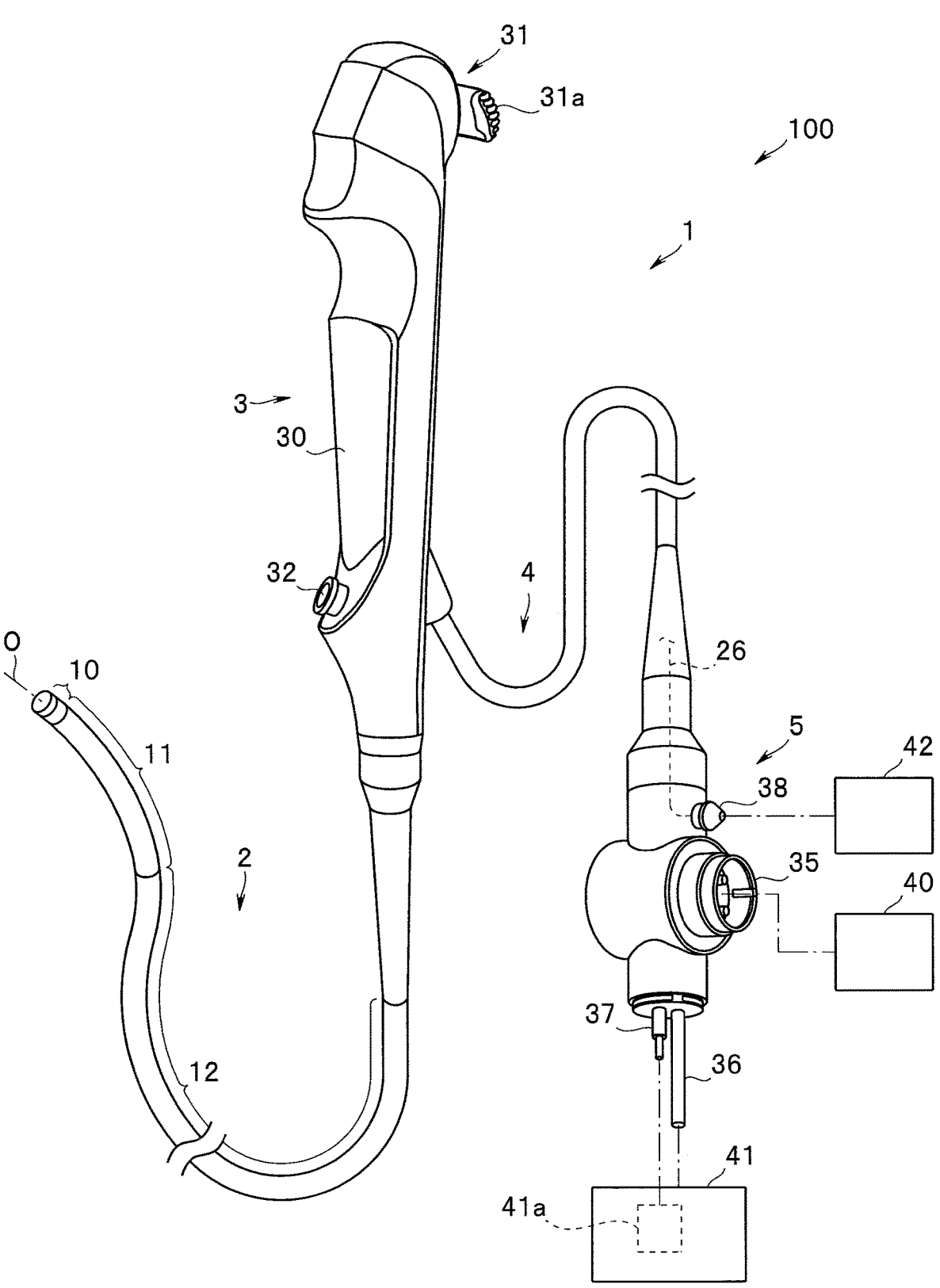
FIG. 1 relates to a first embodiment and is a perspective view showing an exterior of an endoscope.

A first embodiment of the present disclosure is explained below with reference to FIGS. 1 to 7. FIG. 1 is a perspective view showing an exterior of an endoscope. Note that, in the present embodiment, a configuration of the endoscope is explained as an example of a configuration of an insertion instrument.

An endoscope 1 shown in FIG. 1 is a ureteropelvic endoscope. Further, the endoscope 1 is a single-use endoscope that is discarded (disposed of) after a single use. Note that the endoscope 1 may be a reuse endoscope that is disinfected and sterilized after use and reused.

The endoscope 1 includes an insertion portion (insertion section) 2, an operation portion 3, a universal cable 4, and an endoscope connector 5.

The insertion portion 2 includes, in order from a distal end side in a longitudinal direction O, a distal end constituting portion (a distal end portion) 10, a bending portion 11, and a flexible tube portion 12.

Figure 2:
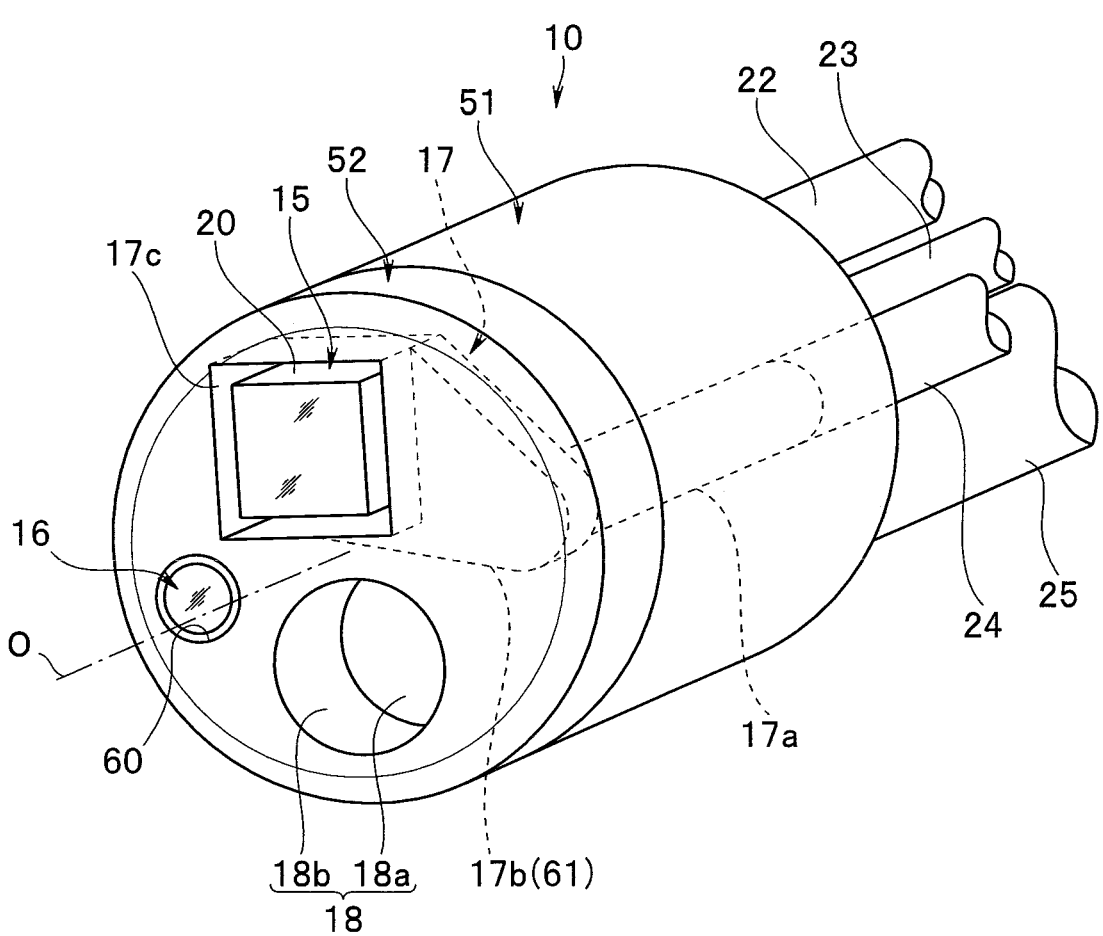
FIG. 2 relates to the first embodiment and is a perspective view showing a distal end constituting member from a distal end side.
Figure 3:
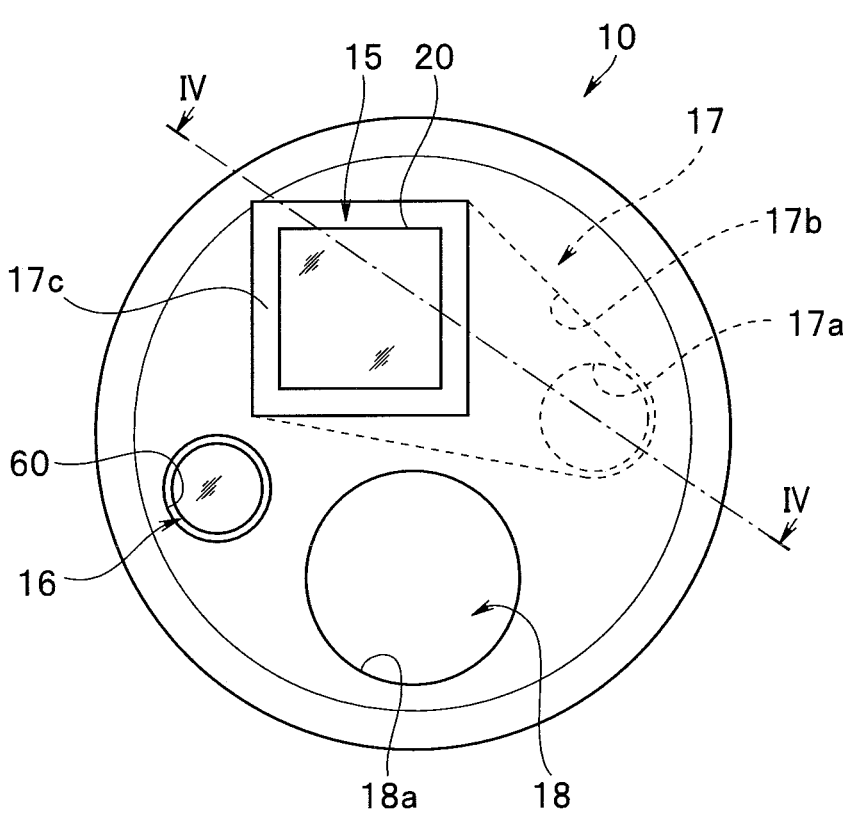
FIG. 3 relates to the first embodiment and is a plan view of the distal end constituting member.

As shown in FIGS. 2 and 3, for example, an image pickup unit 15, an illumination optical unit 16, a gas feeding and liquid feeding flow path 17, and a treatment instrument insertion hole (suctioning channel) 18 are provided in the distal end constituting portion 10.

Figure 4:
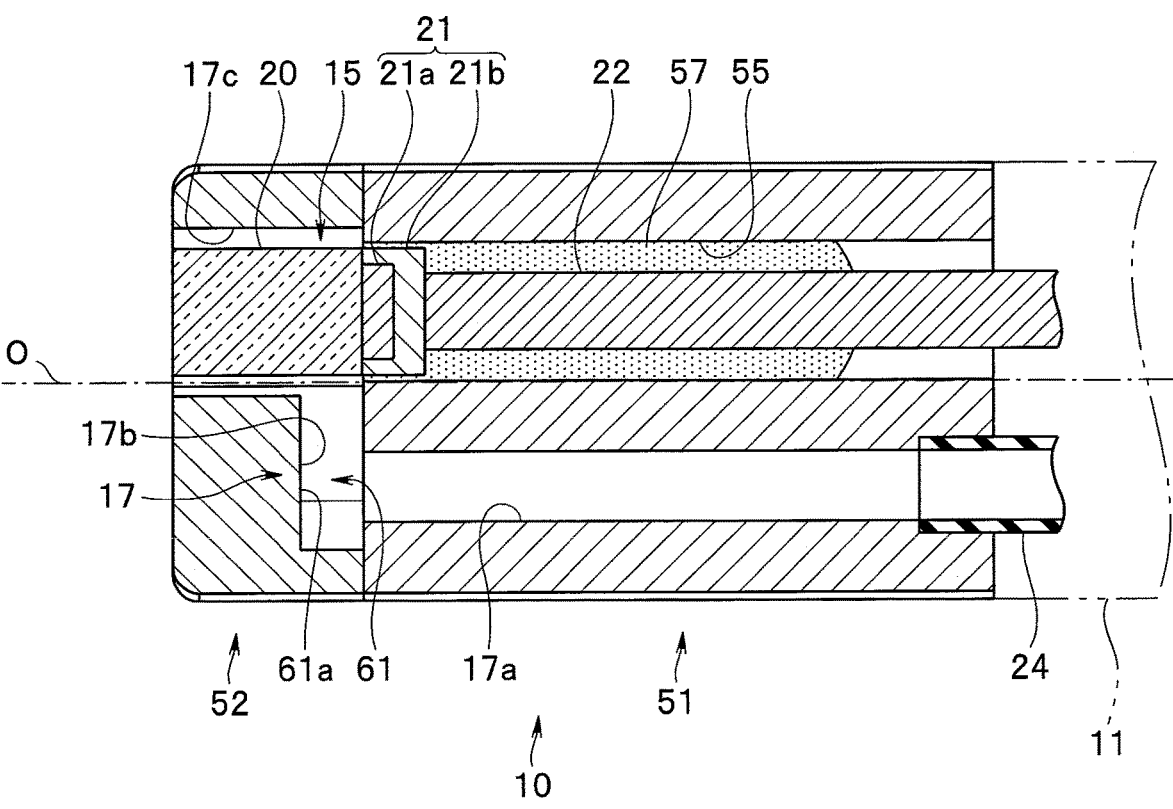
FIG. 4 relates to the first embodiment and is a Iv-Iv sectional view of FIG. 3.
Figure 5:
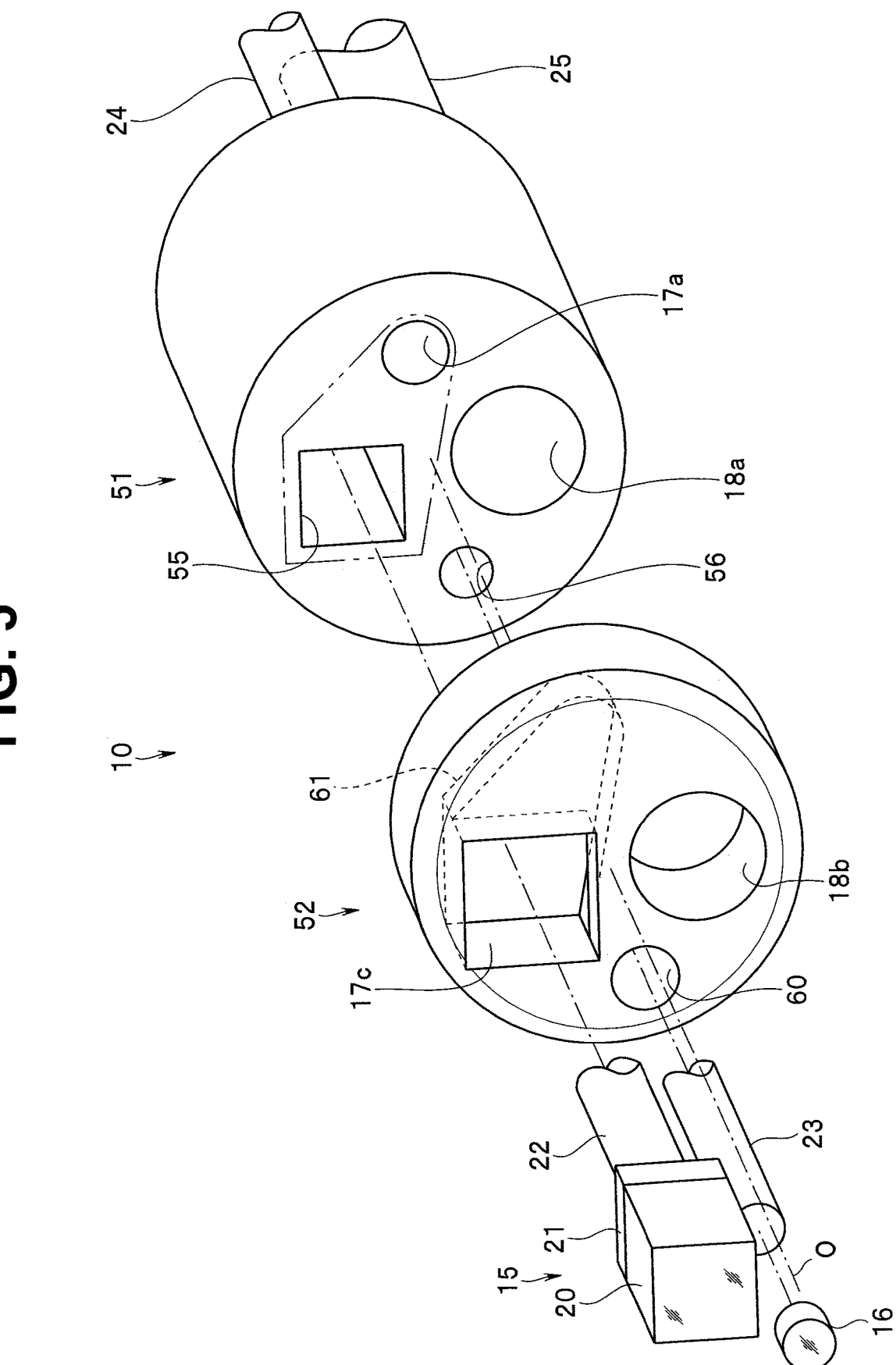
FIG. 5 relates to the first embodiment and is an exploded perspective view of a distal end constituting portion.

As shown in FIGS. 4 and 5, the image pickup unit 15 includes an objective optical unit 20 functioning as an objective optical system and an image pickup device unit 21. The objective optical unit 20 may include an objective lens. The distal end portion 10 includes an opening in a distal end surface of the distal end portion. The opening may extend from the distal end surface toward a proximal end of the distal end portion 10. The distal end portion 10 includes the objective lens located in the opening. The objective lens has a field of view.

The objective optical unit 20 may be configured by, for example, a stacked body (a stacked lens) of a plurality of objective lenses. The objective optical unit 20 is manufactured by, for example, cutting out an individual piece of the stacked lens with dicing or the like from a glass substrate in which a plurality of stacked lenses is formed. Therefore, a plan-view shape of the objective optical unit 20 in the present embodiment is formed in a rectangular shape.

The image pickup device unit 21 includes an image pickup device 21a and a circuit board 21b.

The image pickup device 21a is connected to the objective optical unit 20. An image of a subject is formed on a light receiving surface of the image pickup device 21a via the objective optical unit 20. Consequently, the image pickup device 21a is capable of picking up an optical image of an inside of the subject acquired by the objective optical unit 20.

The image pickup device 21a is implemented on the circuit board 21b. Various signal cables are connected to the circuit board 21b as wirings. The various signal cables are bundled by a coat or the like and configure a signal cable bundle 22. The signal cable bundle 22 is extended toward a proximal end side of the insertion portion 2 from the image pickup unit 15 (the circuit board 21b).

Note that a plan view shape of the circuit board 21b in the present embodiment is formed in a rectangular shape the same as the plan view shape of the objective optical unit 20. Consequently, an overall shape of the image pickup unit 15 is formed in a square pillar shape.

The bending portion 11 has, for example, a configuration capable of actively bending the insertion portion 2 in upward and downward two directions (UP-DOWN). Note that the bending portion 11 is not limited to the configuration capable of actively bending in the upward and downward two directions. For example, the bending portion 11 may be configured to be capable of bending in four directions including left and right directions in addition to the upward and downward directions. The bending portion 11 may be configured to be capable of bending, for example, only in the upward direction.

The upward and downward directions and the left and right directions in the insertion portion 2 are defined in association with, for example, upward and downward directions and left and right directions of an image picked up by the image pickup unit 15.

The flexible tube portion 12 is configured by, for example, a tubular member capable of passively bending with an external force. For example, the signal cable bundle 22, a light guide bundle 23, a gas feeding and liquid feeding channel 24, a treatment instrument channel 25, and the like are inserted through an inside of the flexible tube portion 12.

The light guide bundle 23 is an optical member for guiding illumination light to the illumination optical unit 16. Therefore, the illumination optical unit 16 is optically connected to the distal end side of the light guide bundle 23.

The gas feeding and liquid feeding channel 24 is a channel for supplying fluid (gas or liquid) to the gas feeding and liquid feeding flow path 17 of the distal end constituting portion 10. Therefore, the distal end side of the gas feeding and liquid feeding channel 24 is connected to the proximal end side of the gas feeding and liquid feeding flow path 17.

The treatment instrument channel 25 is a channel for guiding a treatment instrument and the like to the treatment instrument insertion hole 18. Therefore, the distal end side of the treatment instrument channel 25 is connected to the proximal end side of the treatment instrument insertion hole 18. Note that, in the present embodiment, the treatment instrument channel 25 also includes a function of an opening portion for suctioning fluid and the like in the subject.

For example, a grasping portion 30, a bending operation portion 31, and a pipe sleeve 32 are provided in the operation portion 3.

The grasping portion 30 is formed in a shape with which a user is capable of grasping the grasping portion 30 with a hand when using the endoscope 1.

The bending operation portion 31 is provided, for example, on the proximal end side relative to the grasping portion 30. For example, a bending operation lever 31a formed in a L shape is provided in the bending operation portion 31. The bending operation lever 31a is capable of turning around a not-shown rotation axis. The user is capable of, by performing turning operation for the bending operation lever 31*a*, causing the bending portion 11 to perform a bending operation in the upward and downward directions.

The pipe sleeve 32 is provided on the distal end side relative to the grasping portion 30. Inside the operation portion 3, the proximal end side of the treatment instrument channel 25 is connected to the pipe sleeve 32. Consequently, the pipe sleeve 32 is caused to communicate with the treatment instrument insertion hole 18 via the treatment instrument channel 25.

The universal cable 4 is extended from the operation portion 3, for example, on the distal end side relative to the grasping portion 30. For example, the signal cable bundle 22, the light guide bundle 23, the gas feeding and liquid feeding channel 24, and a suction channel 26 (see FIG. 1) are inserted through the universal cable 4.

Note that the distal end side of the suction channel 26 is connected to the treatment instrument channel 25 inside the operation portion 3. Consequently, the suction channel 26 is caused to communicate with the treatment instrument insertion hole 18 via the treatment instrument channel 25. The treatment instrument channel 25 and the suction channel 26 realize a function of a discharge tube for feeding liquid retained in the subject to an outside of the subject.

The endoscope connector 5 is connected to an extension end of the universal cable 4. The endoscope connector 5 includes, for example, an electric connector 35, a light source connector 36, a gas feeding and liquid feeding plug 37, and a suction pipe sleeve 38.

The electric connector 35 is provided, for example, in a side portion of the endoscope connector 5. Inside the endoscope connector 5, the signal cable bundle 22 is connected to the electric connector 35. The electric connector 35 is connectable to, for example, a video processor 40 (see FIG. 1), which is external equipment.

The light source connector 36 is provided, for example, at an end portion of the endoscope connector 5. Inside the endoscope connector 5, the light guide bundle 23 is connected to the light source connector 36. The light source connector 36 is connectable to, for example, a light source apparatus 41 (see FIG. 1), which is external equipment.

The gas feeding and liquid feeding plug 37 is provided, for example, at an end portion of the endoscope connector 5. Inside the endoscope connector 5, the gas feeding and liquid feeding channel 24 is connected to the gas feeding and liquid feeding plug 37. The gas feeding and liquid feeding plug 37 is connectable to, for example, a gas feeding and liquid feeding apparatus 41*a*, which is external equipment.

The suction pipe sleeve 38 is provided, for example, in a side portion of the endoscope connector 5. Inside the endoscope connector 5, a suction tube is connected to the suction pipe sleeve 38. The suction pipe sleeve 38 is connectable to, for example, a suction apparatus 42 (see FIG. 1), which is external equipment.

By being connected to the various kinds of external equipment via the endoscope connector 5 as explained above, the endoscope 1 configures an endoscope system 100 that perfuses fluid (gas and liquid) between the inside and the outside of the subject. Note that the endoscope connector 5 may be configured to be connected to external equipment via an adapter, which is a not-shown intermediate connection body.

Subsequently, a specific configuration of the distal end constituting portion 10 is explained with reference to FIGS. 2 to 6.

As shown in FIGS. 2 and 5, the distal end constituting portion 10 includes a first distal end constituting member (first distal end member) 51 and a second distal end constituting member (second distal end member) 52.

The first distal end constituting member 51 is formed in a columnar shape. The proximal end side of the first distal end constituting member 51 is connected to the bending portion 11 (see FIGS. 1 and 4).

As shown in FIG. 5, an image pickup unit holding hole (opening or imaging channel) 55 functioning as a holding hole, a light guide holding hole 56, a first flow path (first conduit) 17*a*, and a first treatment instrument insertion hole (second opening) 18*a* are provided in the first distal end constituting member 51.

The image pickup unit holding hole 55 is configured by, for example, a rectangular hole that penetrates through the first distal end constituting member 51. The image pickup unit holding hole 55 extends in the longitudinal direction O of the insertion portion 2. As shown in FIG. 4, for example, the image pickup device unit 21 and the signal cable bundle 22 are inserted through the image pickup unit holding hole 55.

Further, an adhesive 57 is charged in the image pickup unit holding hole 55. The image pickup device unit 21 and the signal cable bundle 22 are bonded and fixed to an inside of the image pickup unit holding hole 55 by the adhesive 57. The objective optical unit 20 is fixed to the first distal end constituting member 51 (the distal end constituting portion 10) via the image pickup device unit 21 and the signal cable bundle 22. In addition, the image pickup device unit 21 and the signal cable bundle 22 adhere to the image pickup unit holding hole 55, whereby the image pickup unit holding hole 55 is sealed. Inflow of fluid into the proximal end side of the image pickup unit holding hole 55 is prevented by the sealing.

Note that the objective optical unit 20 may be fixed to the first distal end constituting member 51 via at least one of the image pickup device unit 21 or the signal cable bundle 22.

The light guide holding hole 56 is configured by, for example, a circular hole that penetrates through the first distal end constituting member 51. The light guide holding hole 56 extends in the longitudinal direction O of the insertion portion 2. The light guide bundle 23 is inserted through the light guide holding hole 56. The light guide bundle 23 is fixed to the first distal end constituting member 51 via an adhesive.

The first flow path 17*a* is configured by, for example, a circular hole that penetrates through the first distal end constituting member 51. The first flow path 17*a* extends in the longitudinal direction O of the insertion portion 2. The first flow path 17*a* configures the proximal end side of the gas feeding and liquid feeding flow path 17. Therefore, as shown in FIG. 4, a distal end portion of the gas feeding and liquid feeding channel 24 is connected to a proximal end portion of the first flow path 17*a*. An inner diameter of the first flow path 17*a* is set to be the same diameter as an inner diameter of the gas feeding and liquid feeding channel 24. In other words, an opening area (a flow path sectional area) of the first flow path 17*a* is set to be the same as an opening area (a flow path sectional area) of the gas feeding and liquid feeding channel 24.

The first treatment instrument insertion hole 18*a* is configured by, for example, a circular hole that penetrates through the first distal end constituting member 51. The first treatment instrument insertion hole 18*a* extends in the longitudinal direction O of the insertion portion 2. The first treatment instrument insertion hole 18*a* configures the proximal end side of the treatment instrument insertion hole 18. Therefore, a distal end portion of the treatment instrument channel 25 is connected to a proximal end portion of the first treatment instrument insertion hole 18*a*.

The second distal end constituting member 52 is formed in a columnar shape. An outer diameter of the second distal end constituting member 52 is set to the same diameter as an outer diameter of the first distal end constituting member 51. A proximal end face of the second distal end constituting member 52 is fixed to a distal end face of the first distal end constituting member 51 by bonding.

As shown in FIGS. 3 to 6, an optical unit holding hole 60, a guide groove 61, a third flow path (third conduit) 17*c* functioning as a discharge port, and a second treatment instrument insertion hole 18*b* are provided in the second distal end constituting member 52.

The first flow path 17*a*, the second flow path 17*b*, and the third flow path 17*c* form a flow path. The flow path includes a first flow path section located in the first flow path 17*a*, a second flow path section located in the second flow path 17*b*, and a third flow path section located in the third flow path 17*b*.

The optical unit holding hole 60 is configured by, for example, a circular hole that penetrates through the second distal end constituting member 52. The optical unit holding hole 60 extends in the longitudinal direction O of the insertion portion 2. Further, the optical unit holding hole 60 is disposed in a position in line with the light guide holding hole 56.

The illumination optical unit 16 is inserted into the distal end side of the optical unit holding hole 60. The illumination optical unit 16 is fixed to the second distal end constituting member 52 via an adhesive.

A distal end portion of the light guide bundle 23 is inserted into the proximal end side of the optical unit holding hole 60. Consequently, the illumination optical unit 16 is optically connected to the light guide bundle 23.

Figure 6:
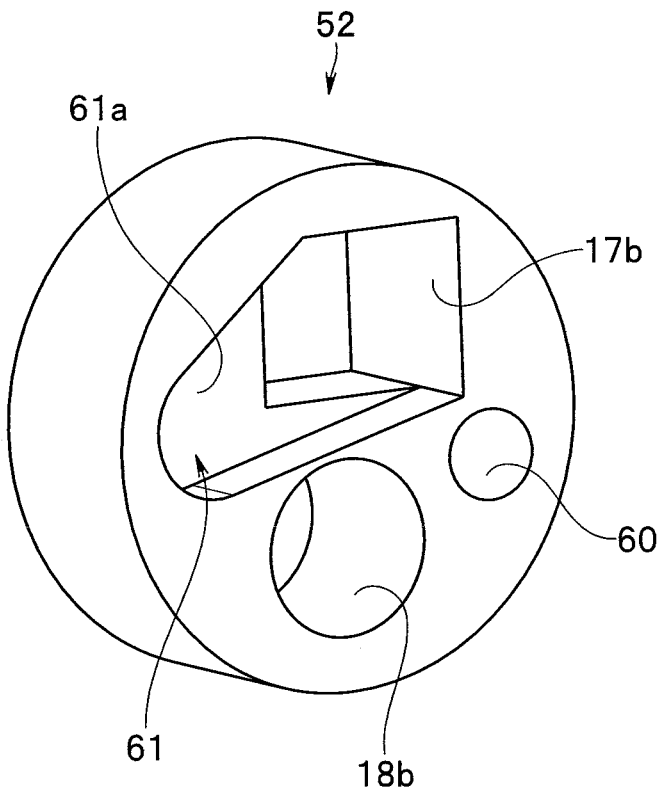
FIG. 6 relates to the first embodiment and is a perspective view showing a first distal constituting member from a proximal end side.

As shown in FIG. 6, the guide groove 61 is provided on the proximal end side of the second distal end constituting member 52. The guide groove 61 is configured by a concave groove recessed by a predetermined depth from the proximal end face of the second distal end constituting member 52 toward the distal end side. The guide groove 61 extends from the first flow path 17*a* side to the image pickup unit holding hole 55 side, for example, as indicated by an alternate long and two short dashes line.

As shown in FIG. 4, when the second distal end constituting member 52 is fixed to the first distal end constituting member 51, the guide groove 61 forms a second flow path (second conduit) 17*b* between the guide groove 61 and a distal end face of the first distal end constituting member 51. An upstream side of the second flow path 17*b* is connected to a downstream end of the first flow path 17*a*. Consequently, the second flow path 17*b* configures a halfway part of the gas feeding and liquid feeding flow path 17. The first conduit 17*a* extends in the longitudinal direction. The second conduit 17*b* is connected to the first conduit 17*a*. The second conduit 17*b* extends in a direction other than the longitudinal direction. The second conduit 17*b* is located distally relative to the first conduit 17*a*. A space between a side surface of the objective lens and a side surface of the opening in the distal end surface may define the third conduit 17*c*. The third conduit connects to the second conduit 17*b*. The second conduit 17*b* may be formed by the distal end surface of the first distal end member 51 and a recess in the proximal end surface of the second distal end member 52.

The second flow path 17*b* is the flow path for feeding fluid passed through the first flow path 17*a* in a direction crossing the longitudinal direction O of the insertion portion 2. The second flow path 17*b* in the present embodiment causes, for example, the fluid passed through the first flow path 17*a* to flow in a direction orthogonal to the longitudinal direction O of the insertion portion 2. A downstream side of the second flow path 17*b* is set toward the image pickup unit 15 held by the image pickup unit holding hole 55.

A part of a wall (wall section) 61*a* forming a bottom portion of the guide groove 61 faces the downstream end of the first flow path 17*a*. A fluid flowing in the first flow path section contacts the wall section 61*a* and changes direction to flow in the second flow path section.

A groove width of the guide groove 61 is set to gradually increase from the first flow path 17*a* side toward the image pickup unit holding hole 55 side. Consequently, an opening area (a flow path sectional area) of the second flow path 17*b* is set to gradually change from the upstream side toward the downstream side. More specifically, the flow path sectional area of the second flow path 17*b* is set to gradually increase from the first flow path 17*a* side toward the image pickup unit holding hole 55 side. In this case, the flow path sectional area of the second flow path 17*b* is set larger than the flow path sectional area of the first flow path 17*a* in an entire region from the upstream side to the downstream side of the second flow path 17*b*. A cross-sectional area of the second conduit at the upstream end can be defined as a first cross-sectional area. A cross-sectional area of the second conduit at the downstream end can be defined as a second cross-sectional area. The first cross-sectional area is different from the second cross-sectional area.

The third flow path 17*c* is configured by, for example, a rectangular hole that penetrates through the second distal end constituting member 52. The third flow path 17*c* extends in the longitudinal direction O of the insertion portion 2. On the proximal end side of the second distal end constituting member 52, a downstream end of the guide groove 61 (the second flow path 17*b*) is connected to the third flow path 17*c*. Consequently, the third flow path 17*c* configures the downstream side of the gas feeding and liquid feeding flow path 17. In the present embodiment, for example, as shown in FIGS. 3 and 6, a downstream end of the second flow path 17*b* is connected to the third flow path 17*c* in regions corresponding to two walls among four walls forming the third flow path 17*c*.

Further, the third flow path 17*c* is disposed in a position in line with the image pickup unit holding hole 55. Consequently, the objective optical unit 20 of the image pickup unit 15 fixed to the image pickup unit holding hole 55 is disposed inside the third flow path 17*c*.

Further, the third flow path 17*c* is longitudinally offset relative to the first flow path 17*a*.

An opening area (an opening area in the direction orthogonal to the longitudinal direction O) of the third flow path 17*c* is set larger than a sectional area (a sectional area in the direction orthogonal to the longitudinal direction O) of the objective optical unit 20. Consequently, a gap (space) is formed between an inner circumferential surface of the third flow path 17*c* and an outer circumferential surface of the objective optical unit 20. An area in the direction orthogonal to the longitudinal direction O of the gap (a substantial flow path sectional area of the third flow path 17*c*) is set to be larger than the opening area (the flow path sectional area) of the first flow path 17*a*. In other words, the opening area of the third flow path 17*c* is set such that a value obtained by subtracting the sectional area of the objective optical unit 20 from the opening area of the third flow path 17c is larger than the opening area of the first flow path 17a.

The second treatment instrument insertion hole 18b is configured by, for example, a circular hole that penetrates through the second distal end constituting member 52. The second treatment instrument insertion hole 18b extends in the longitudinal direction O of the insertion portion 2. Further, the second treatment instrument insertion hole 18b is disposed in a position in line with the first treatment instrument insertion hole 18a. Consequently, the second treatment instrument insertion hole 18b configures the treatment instrument insertion hole 18 in conjunction with the first treatment instrument insertion hole 18a.

The endoscope 1 configured as explained above is capable of performing perfusion for inflating an inside of a body cavity (a lumen in the subject) to secure a visual field in the body cavity (in the lumen) and discharging solid matter pieces and the like in the body cavity (the lumen) to an outside of a body. At a perfusion time, for example, fluid (liquid) such as saline is supplied to the distal end constituting portion 10 via the gas feeding and liquid feeding channel 24. The fluid supplied to the distal end constituting portion 10 is discharged into the body cavity via the gas feeding and liquid feeding flow path 17. A part of the fluid retained in the body cavity is suctioned from the treatment instrument insertion hole 18. The fluid suctioned from the treatment instrument insertion hole 18 is discharged to the outside of the body via the treatment instrument channel 25 and the suction channel.

At such a perfusion time, the fluid supplied from the gas feeding and liquid feeding channel 24 to the gas feeding and liquid feeding flow path 17 is discharged into the body cavity (the lumen in the subject) after flow velocity of the fluid is reduced by the gas feeding and liquid feeding flow path 17. Further, the fluid discharged from the gas feeding and liquid feeding flow path 17 cleans the objective optical unit 20.

Figure 7:
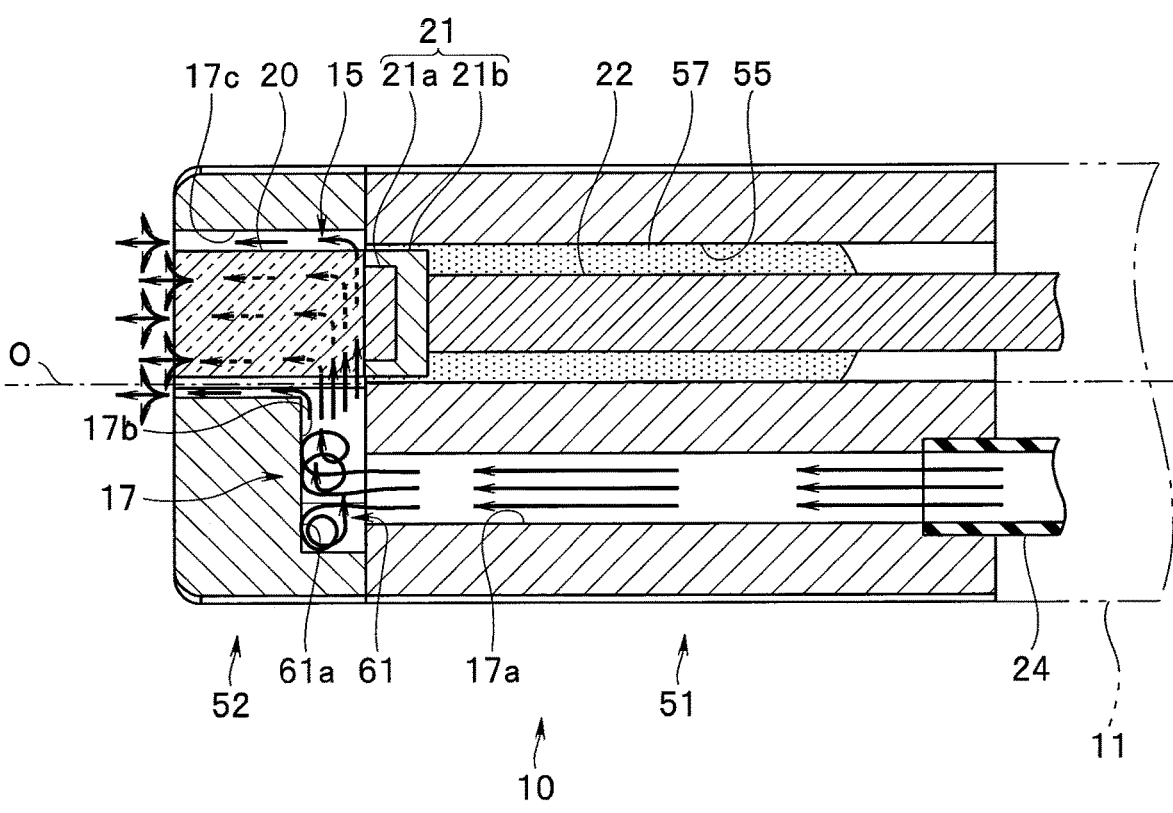
FIG. 7 relates to the first embodiment and is an explanatory view showing behavior of fluid in the distal end constituting portion.

More specifically, for example, as shown in FIG. 7, in the present embodiment, the first flow path 17a is extended in the longitudinal direction O like the gas feeding and liquid feeding channel 24. The flow path sectional area of the first flow path 17a is set to be the same as the flow path sectional area of the gas feeding and liquid feeding channel 24. Therefore, the fluid flowing into the first flow path 17a from the gas feeding and liquid feeding channel 24 passes through the first flow path 17a at the same flow velocity without being decelerated.

The fluid passed through the first flow path 17a flows into the second flow path 17b. The wall 61a of the guide groove 61 forming the second flow path 17b faces the downstream end of the first flow path 17a. The fluid immediately after flowing into the second flow path 17b collides with the wall 61a. The fluid is agitated on the upstream side of the second flow path 17b by the collision with the wall 61a. Further, the flow velocity of the fluid is reduced by the agitation of the fluid.

The fluid after colliding with the wall 61a flows to the downstream side of the second flow path 17b along the wall 61a. An extending direction of the second flow path 17b is different from the extending direction of the first flow path 17a. A flowing direction of the fluid flowing into the second flow path 17b from the first flow path 17a is forcibly changed by the difference between the extending directions. Consequently, the fluid is further agitated inside the second flow path 17b.

In addition, the flow path sectional area of the second flow path 17b increases toward the downstream side. Therefore, the fluid agitated on the upstream side of the second flow path 17b is diffused toward the downstream side of the second flow path 17b. The flow velocity of the fluid is gradually reduced toward the downstream side of the second flow path 17b by the diffusion of the fluid.

The fluid passed through the second flow path 17b flows into the third flow path. An extending direction of the third flow path 17c is different from the extending direction of the second flow path 17b. A flowing direction of the fluid flowing into the third flow path 17c from the second flow path 17b is forcibly changed by the difference between the extending directions. Consequently, the fluid is further agitated inside the third flow path 17c.

The fluid agitated inside the third flow path 17c flows around a periphery of the objective optical unit 20 while flowing downstream in the third flow path 17c. In this case, the substantial flow path sectional area of the third flow path 17c is set to be larger than the flow path sectional area of the first flow path 17a. Consequently, the flow velocity of the fluid reduced in the second flow path 17b is maintained at predetermined flow velocity.

The fluid passed through the third flow path 17c is discharged to the inside of the subject at low flow velocity. An internal space of the subject is expanded by the fluid discharged in this way. Consequently, a visual field inside the subject is secured.

In this case, the fluid discharged to the inside of the subject from the third flow path 17c is surrounding a periphery of the objective optical unit 20. Therefore, the objective optical unit 20 is cleaned by the fluid discharged from the second flow path 17c. For example, air bubbles, fractured stones, and the like adhering to the objective optical unit 20 are removed by the fluid discharged from the third flow path 17c. Consequently, a visual field of the objective optical unit 20 is secured.

Note that a part of the fluid retained inside the subject is suctioned from the treatment instrument insertion hole 18. The fluid suctioned from the treatment instrument insertion hole 18 is discharged to the outside of the body via the treatment instrument channel 25 and the suction channel.

Perfusion of the fluid to the inside of the subject is realized by the suction and the discharge of the fluid.

According to the embodiment explained above, the endoscope 1 includes the insertion portion 2 that is inserted into the subject, the distal end constituting portion 10 provided at a distal end in the longitudinal direction O of the insertion portion 2, and the objective optical unit 20 that is provided in the distal end constituting portion 10 and acquires an optical image of the inside of the subject. The distal end constituting portion 10 includes the first flow path 17a extending in the longitudinal direction O, the second flow path 17b that allows the fluid passed through the first flow path 17a to flow in a direction different from the longitudinal direction O, and the third flow path 17c in which the objective optical unit 20 is disposed, the third flow path 17c discharging the fluid passed through the second flow path 17b to an outside of the distal end constituting portion 10 in a direction different from the flowing direction of the fluid by the second flow path 17b. Consequently, it is possible to secure a visual field of an observation window without a flow of the fluid near an observation target of the subject being disturbed by perfusion.

In other words, in the present embodiment, the first to third flow paths 17a to 17c configuring the gas feeding and liquid feeding flow path 17 are connected in a crank shape inside the distal end constituting portion 10. Consequently, the gas feeding and liquid feeding flow path 17 can agitate the fluid supplied from the gas feeding and liquid feeding channel 24 and reduce the flow velocity of the fluid. Therefore, for example, even when the fluid increased in the flow velocity is supplied from the gas feeding and liquid feeding channel 24 reduced in a diameter to the distal end constituting portion 10, it is possible to prevent the fluid from being powerfully jetted to the inside of the subject. Consequently, it is possible to, while securing a flow rate of the fluid supplied to the inside of the subject, prevent an observation target object, a treatment target object, and the like in the subject from greatly moving by, for example, being blown by the fluid.

The objective optical unit 20 is disposed inside the third flow path 17c. Consequently, the third flow path 17c can discharge the fluid to the inside of the subject in a state in which the fluid is dispersed to the periphery of the objective optical unit 20. Therefore, it is possible to more effectively reduce an influence of the fluid supplied into the subject from the third flow path 17c on the observation target object, the treatment target object, and the like in the subject. In addition, the visual field of the observation window can be secured by a distal end face of the objective optical unit 20 being cleaned by the fluid discharged from the periphery of the objective optical unit 20. The fluid dispersed to the periphery of the objective optical unit 20 cools the objective optical unit 20. Consequently, it is possible to accurately prevent a temperature rise of the image pickup device unit 21 connected to the objective optical unit 20.

Further, the third flow path 17c is provided in a position where the objective optical unit 20 is housed inside the third flow path 17c. Consequently, it is possible to efficiently dispose the third flow path 17c and the objective optical unit 20 on a distal end face of the distal end constituting portion 10. Therefore, it is possible to secure the substantial flow path sectional area by the third flow path 17c without increasing the distal end constituting portion 10 in a diameter.

In this case, the objective optical unit 20 is fixed to the distal end constituting portion 10 (the first distal end constituting member 51) via the image pickup device unit 21 and the signal cable bundle 22. Therefore, with a simple configuration, it is possible to dispose the objective optical unit 20 inside the third flow path 17c.

The image pickup device unit 21 and the signal cable bundle 22 are bonded and fixed to the image pickup unit holding hole 55. Consequently, it is possible to seal the image pickup unit holding hole 55. Therefore, even when the objective optical unit 20 is exposed to the fluid inside the third flow path 17c, it is possible to prevent the fluid from intruding to the proximal end side beyond the image pickup unit holding hole 55.

The distal end constituting portion 10 is dividedly formed by the first distal end constituting member 51 and the second distal end constituting member 52. The second flow path 17b is formed between the first distal end constituting member 51 and the second distal end constituting member 52. Consequently, it is possible to easily form the second flow path 17b extending in the direction crossing the longitudinal direction O.

The substantial flow path sectional area of the third flow path 17c (and the flow path sectional area of the second flow path 17b) is set larger than the flow path sectional area of the first flow path 17a. Consequently, it is possible to more accurately reduce the flow velocity of the fluid agitated inside the gas feeding and liquid feeding flow path 17.

The flow path sectional area of the second flow path 17b is set to gradually increase from the upstream side to the downstream side. Consequently, it is possible to evenly reduce the flow velocity of the fluid flowing in the second flow path 17b.

Subsequently, a second embodiment of the present disclosure is explained with reference to FIGS. 8 to 10. The present embodiment is different from the first embodiment explained above in that protrusions for control (surface) 65 for controlling a flow of fluid is provided in the third flow path 17c. Besides, in the present embodiment, the same components as the components in the first embodiment explained above are denoted by the same reference numerals and signs as the reference numerals and signs in the first embodiment and explanation of the components is omitted as appropriate.

Figure 8:
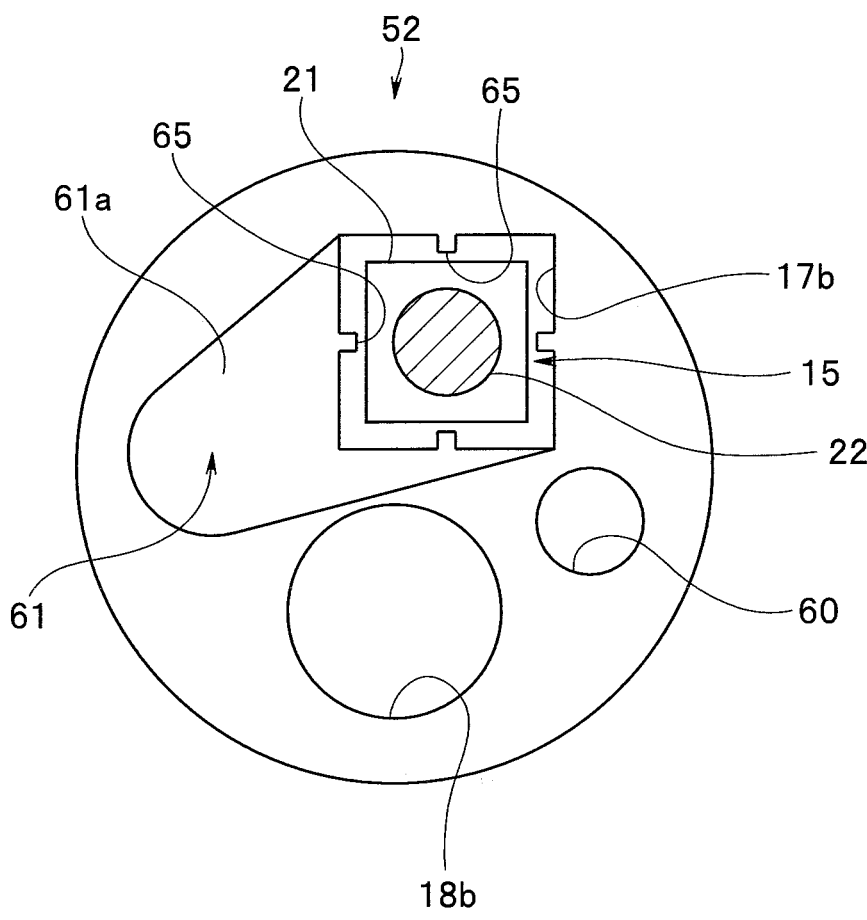
FIG. 8 relates to a second embodiment and is a plan view showing the first distal end constituting member from the proximal end side.
Figure 9:
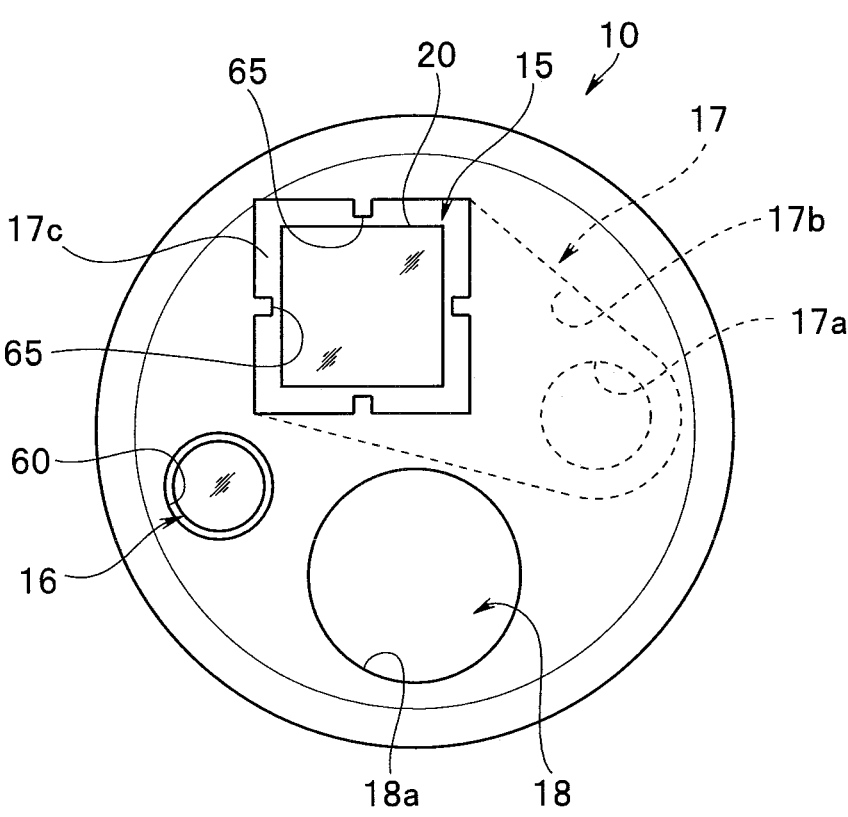
FIG. 9 relates to the second embodiment and is a plan view showing the first distal end constituting member from the distal end side.
Figure 10:
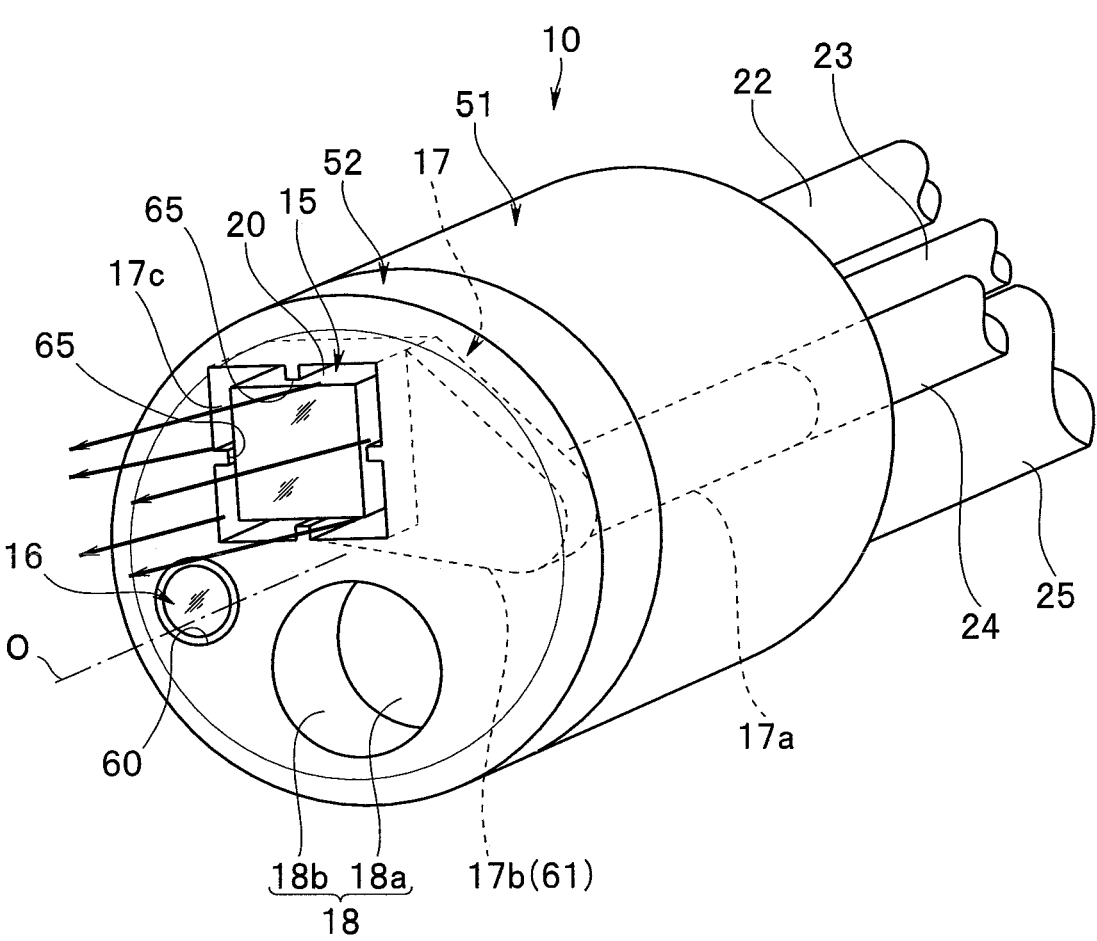
FIG. 10 relates to the second embodiment and is a perspective view showing the distal end constituting member from the distal end side.

As shown in FIGS. 8 to 10, the protrusions for control 65 are respectively provided on the four walls forming the third flow path 17c. The protrusions for control 65 are provided, for example, in centers in width directions of the respective walls. The respective protrusions for control 65 are projected to an inner side of the third flow path 17c. Further, the respective protrusions for control 65 extend in the longitudinal direction O of the third flow path 17c.

According to the embodiment explained above, for example, as shown in FIG. 10, the third flow path 17c can discharge, with the respective protrusions for control 65, the fluid from the periphery of the objective optical unit 20 in a state in which the fluid is rectified in a direction conforming to the longitudinal direction O.

Subsequently, a third embodiment of the present disclosure is explained with reference to FIGS. 11 to 14. The present disclosure is different from the first embodiment explained above in a connection region of the second flow path 17b to the third flow path 17c. Besides, in the present embodiment, the same components as the components in the first embodiment explained above are denoted by the same reference numerals and signs as the reference numerals and signs in the first embodiment and explanation of the components is omitted as appropriate.

Figure 11:
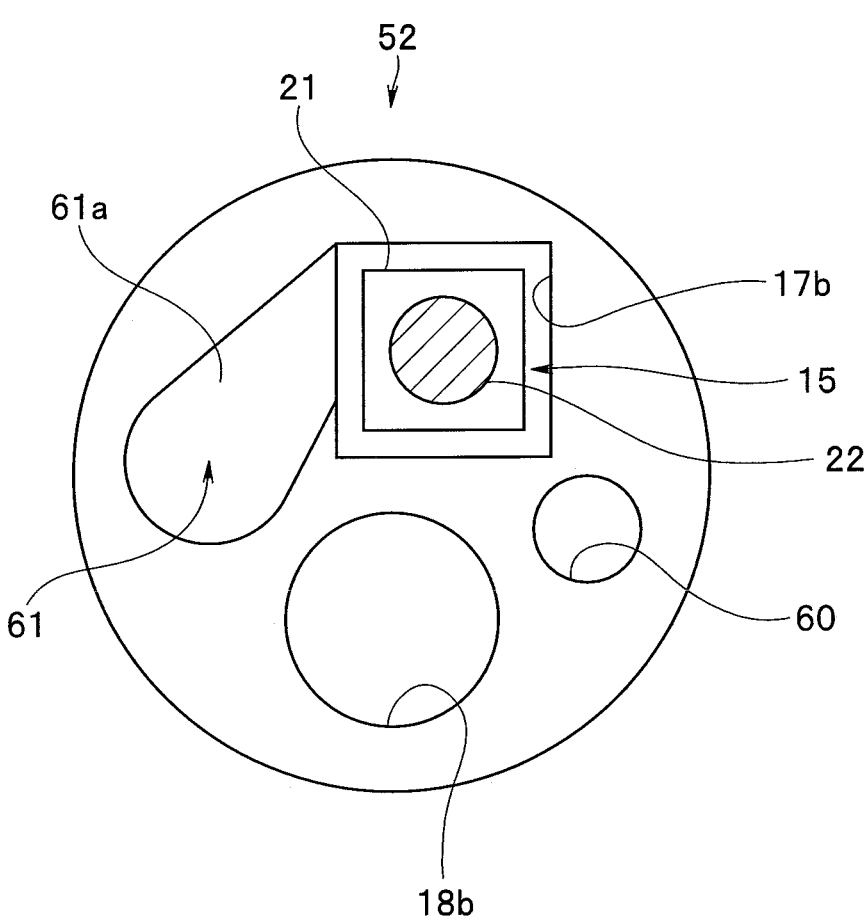
FIG. 11 relates to a third embodiment and is a plan view showing the first distal end constituting member from the proximal end side.
Figure 12:
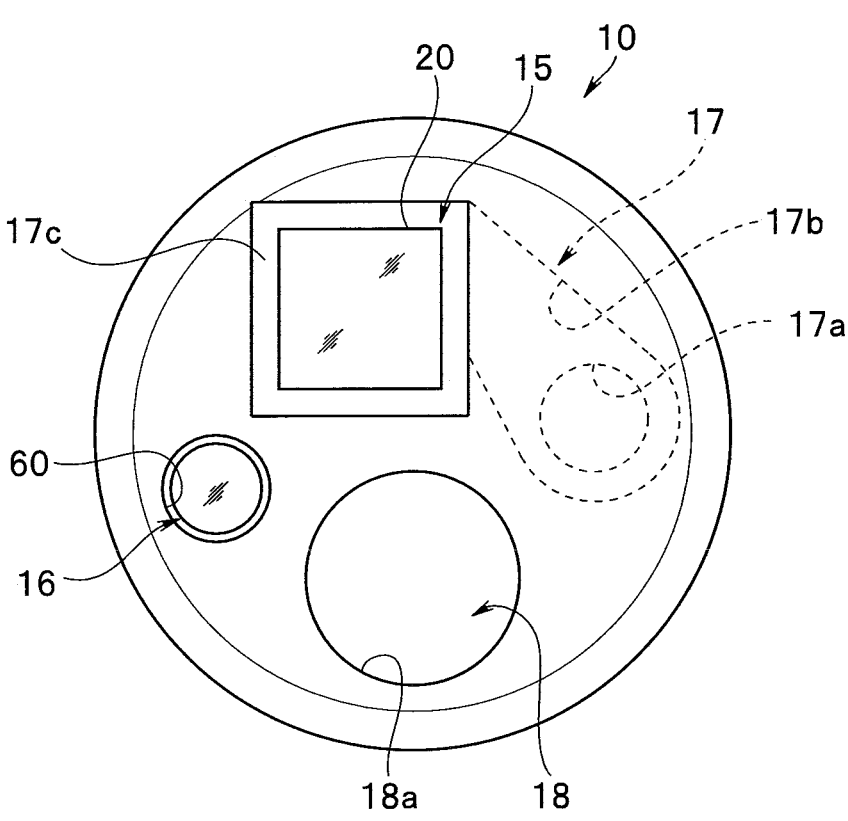
FIG. 12 relates to the third embodiment and is a plan view showing the first distal end constituting member from the distal end side.
Figure 13:
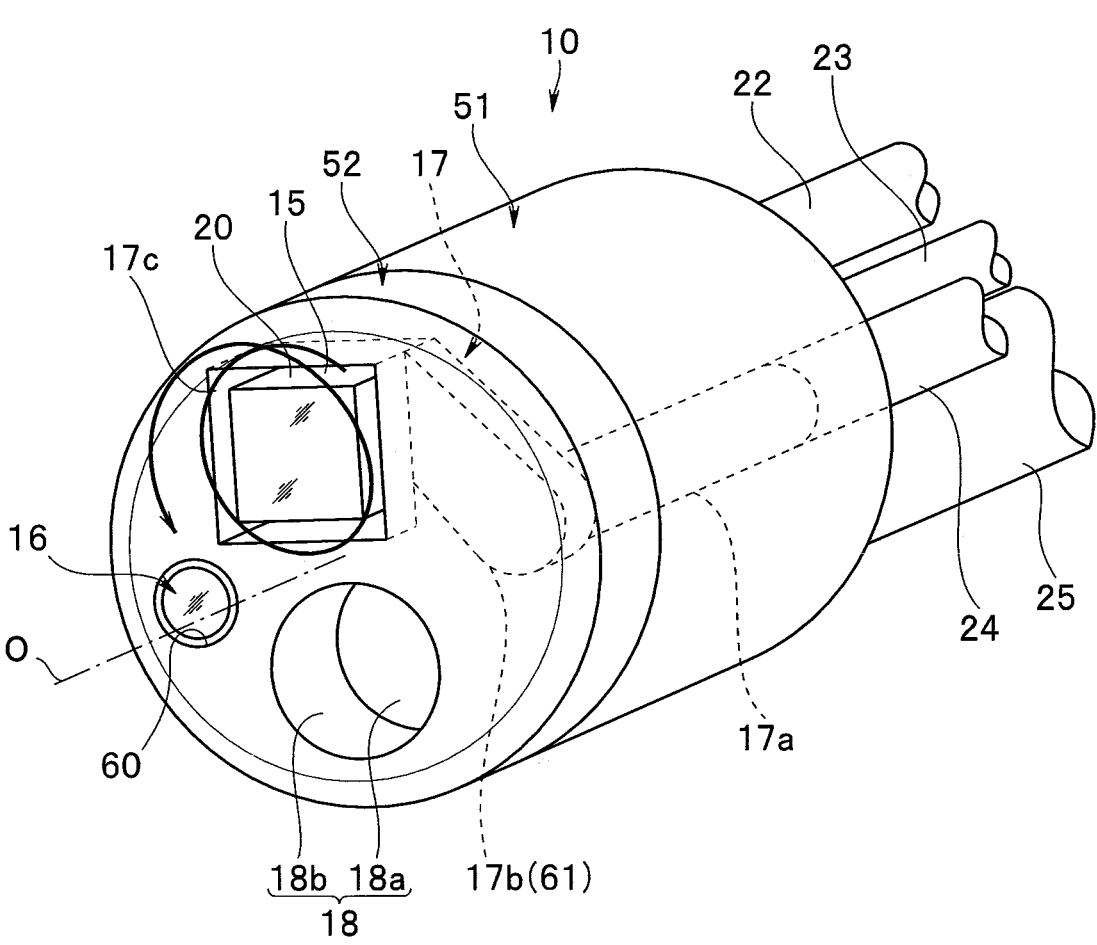
FIG. 13 relates to the third embodiment and is a perspective view showing the distal end constituting member from the distal end side.

As shown in FIGS. 11 to 13, in the present embodiment, the downstream end of the second flow path 17b is connected to the third flow path 17c in a region closer to one side of one wall among the four walls forming the third flow path 17c. Note that, in the present embodiment, the flow path sectional area of the second flow path 17b is set to gradually decrease from the upstream side toward the downstream side of the second flow path 17b.

Figure 14:
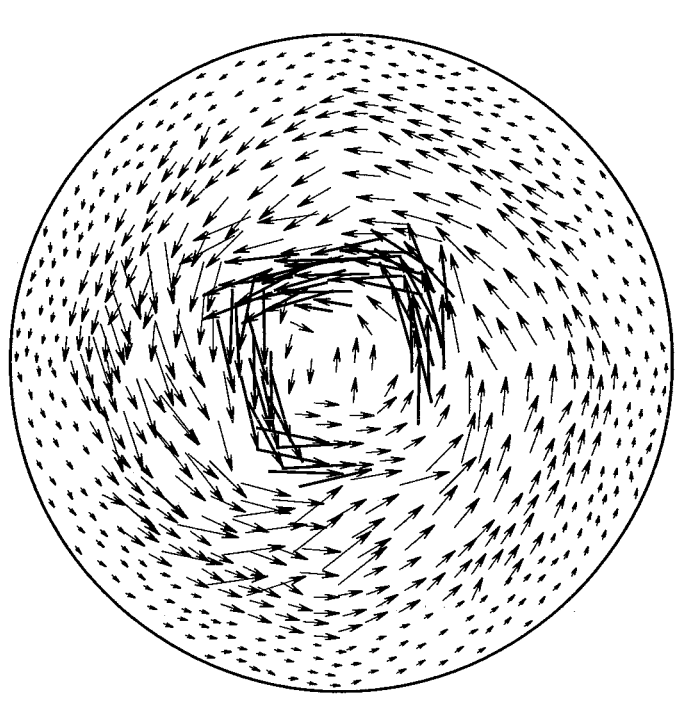
FIG. 14 relates to the third embodiment and is an explanatory view showing a speed distribution of fluid discharged from a discharge port.

According to the embodiment explained above, for example, as shown in FIG. 13, the fluid flowing into the third flow path 17c from the second flow path 17b is discharged to the inside of the subject while spirally turning on an outer periphery of the objective optical unit 20. In other words, for example, as shown in FIG. 14, the fluid discharged from the third flow path 17c forms a vortex flow having low flow velocity. It is possible to effectively clean the distal end face of the objective optical unit 20 with the vortex flow having the low flow velocity. With the vortex flow having the low flow velocity, it is possible to efficiently disperse, to the inside of the subject, the fluid discharged from the third flow path 17c without greatly disturbing the flow of the fluid due to perfusion.

Subsequently, a fourth embodiment of the present disclosure is explained with reference to FIGS. 15 to 17. The present embodiment is different from the first embodiment explained above in that a protective frame 66 surrounding the outer periphery of the objective optical unit 20 is provided. Besides, in the present embodiment, the same components as the components in the first embodiment explained above are denoted by the same reference numerals and signs as the reference numerals and signs in the first embodiment and explanation of the components is omitted as appropriate.

Figure 15:
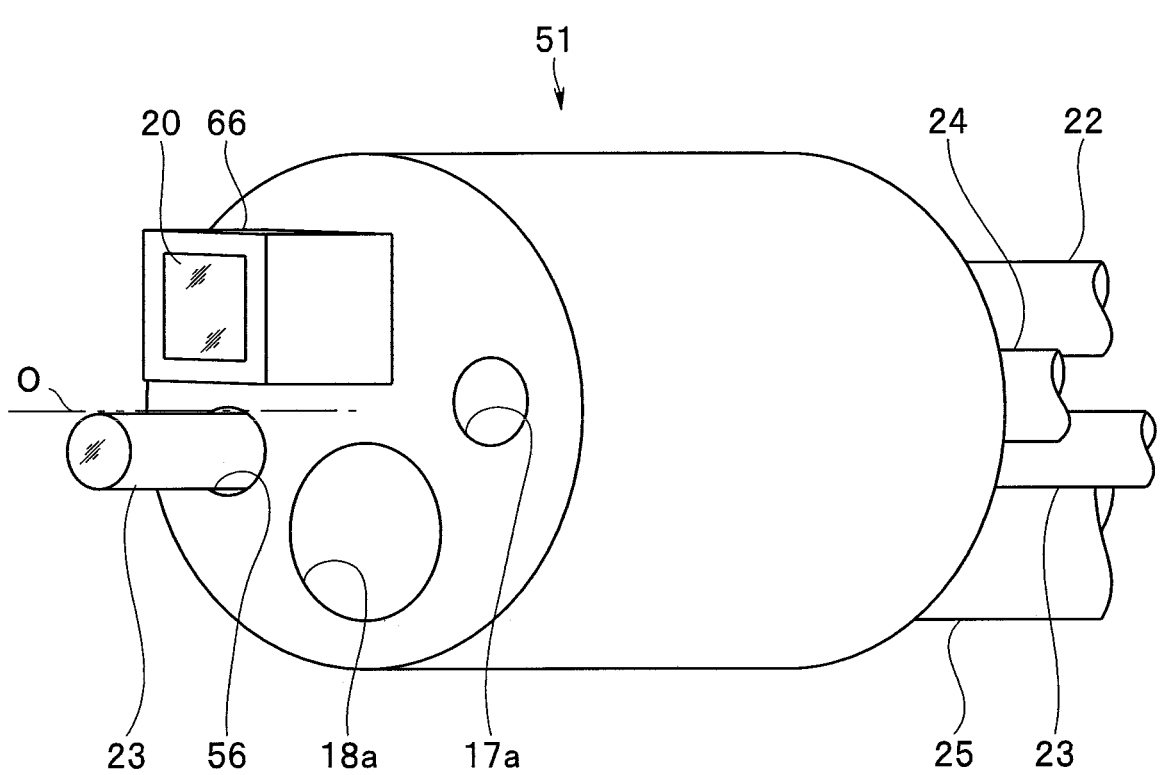
FIG. 15 relates to a fourth embodiment and is a perspective view showing a second distal end constituting member from the distal end side.
Figure 16:
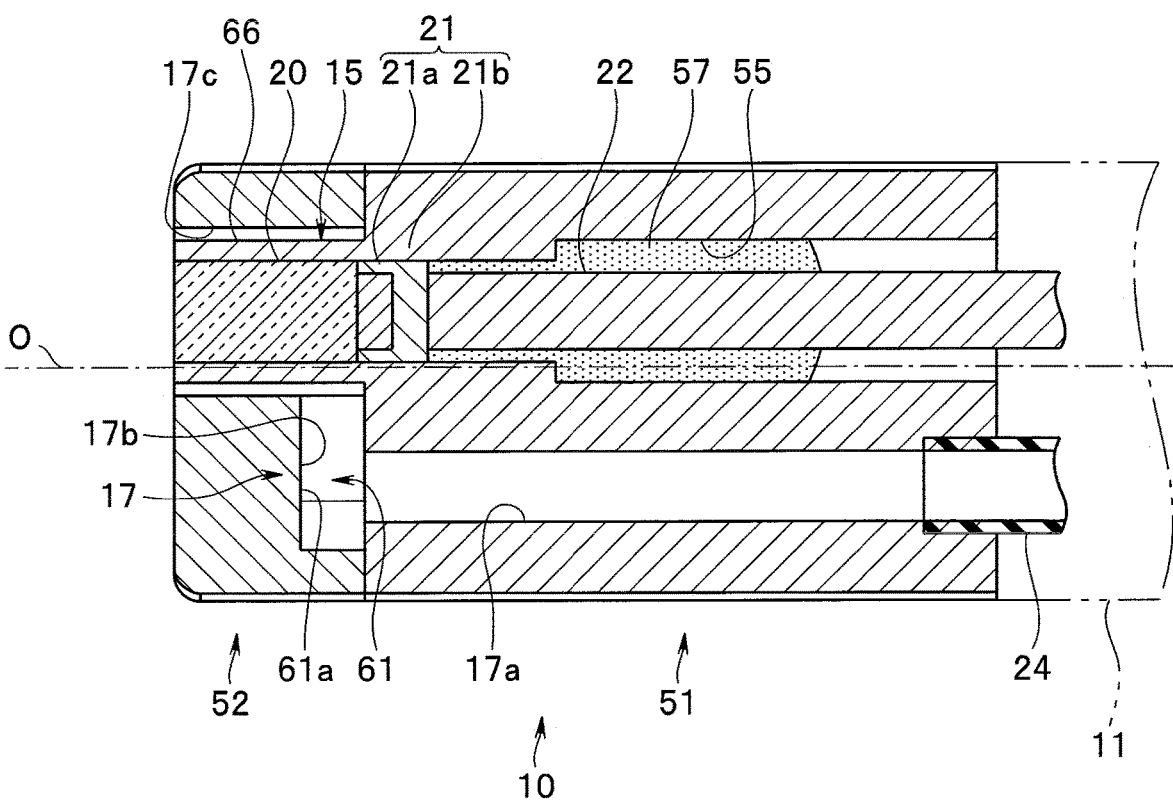
FIG. 16 relates to the fourth embodiment and is a main part sectional view of the distal end constituting member.
Figure 17:
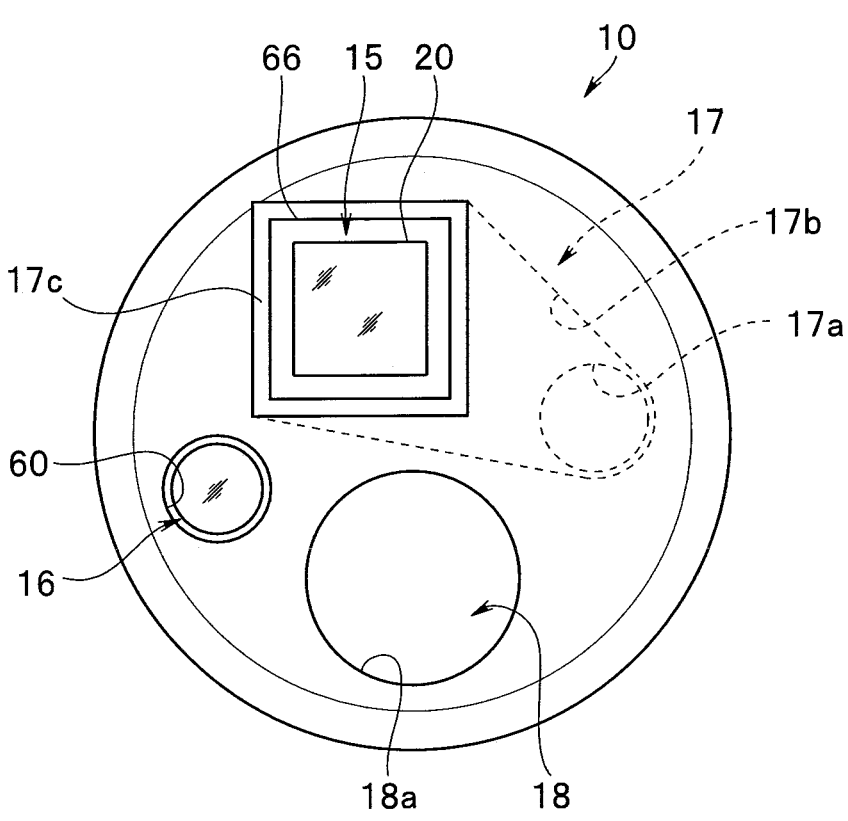
FIG. 17 relates to the fourth embodiment and is a plan view showing the first distal end constituting member from the distal end side.

As shown in FIGS. 15 to 17, the protective frame 66 is projected from the distal end face of the first distal end constituting member 51. The protective frame 66 is provided in a position corresponding to the image pickup unit holding hole 55. The protective frame 66 is formed in a square tube shape for enabling the objective optical unit 20 to be housed inside the protective frame 66.

A gap is formed between the inner circumferential surface of the third flow path 17$c$ and an outer circumferential surface of the protective frame 66. An area in the direction orthogonal to the longitudinal direction O of the gap (the substantial flow path sectional area of the third flow path 17$c$) is set to be larger than the opening area (the flow path sectional area) of the first flow path 17$a$.

For example, as shown in FIG. 16, a length of the protective frame 66 is set to a length capable of surrounding an entire region of the outer circumferential surface of the objective optical unit 20.

The objective optical unit 20 of the image pickup unit 15 held by the image pickup unit holding hole 55 is housed inside the protective frame 66. Further, the objective optical unit 20 housed in the protective frame 66 is bonded and fixed to the protective frame 66 via the adhesive 57.

According to the embodiment explained above, even when the objective optical unit 20 is disposed inside the third flow path 17$c$, it is possible to improve fixing strength of the objective optical unit 20.

Figure 18:
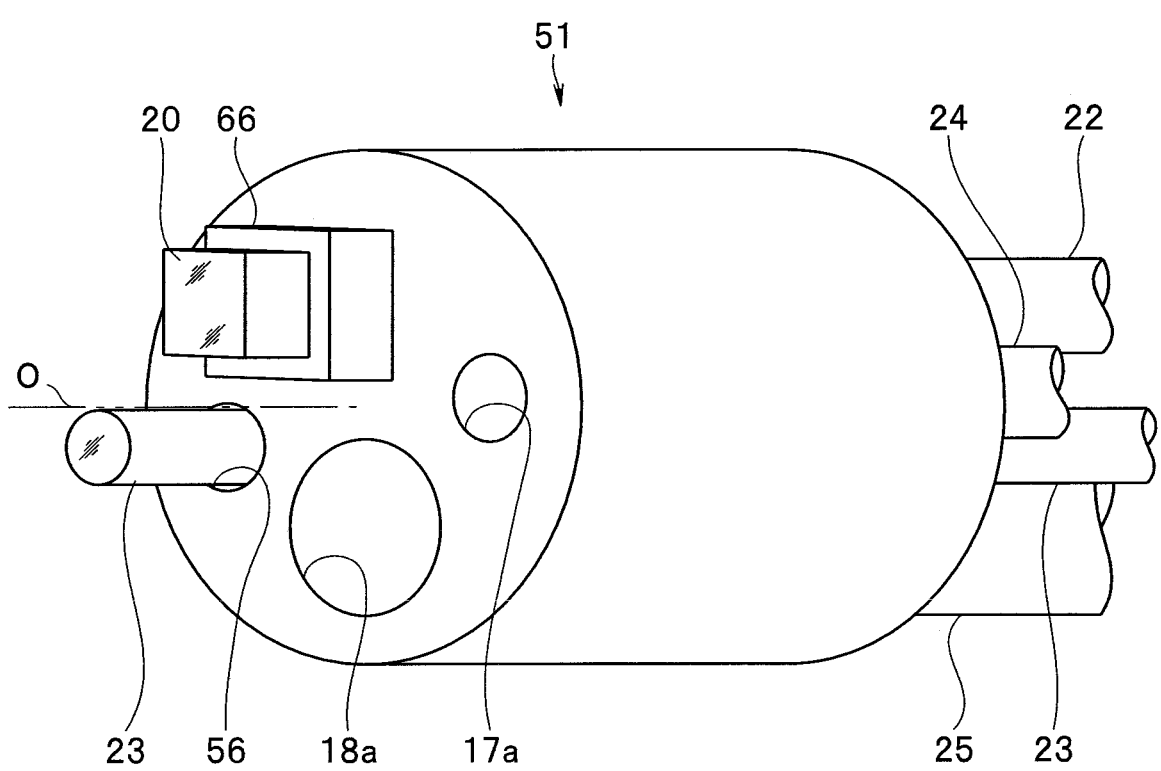
FIG. 18 relates to a modification of the fourth embodiment and is a perspective view showing the second distal end constituting member from the distal end side.
Figure 19:
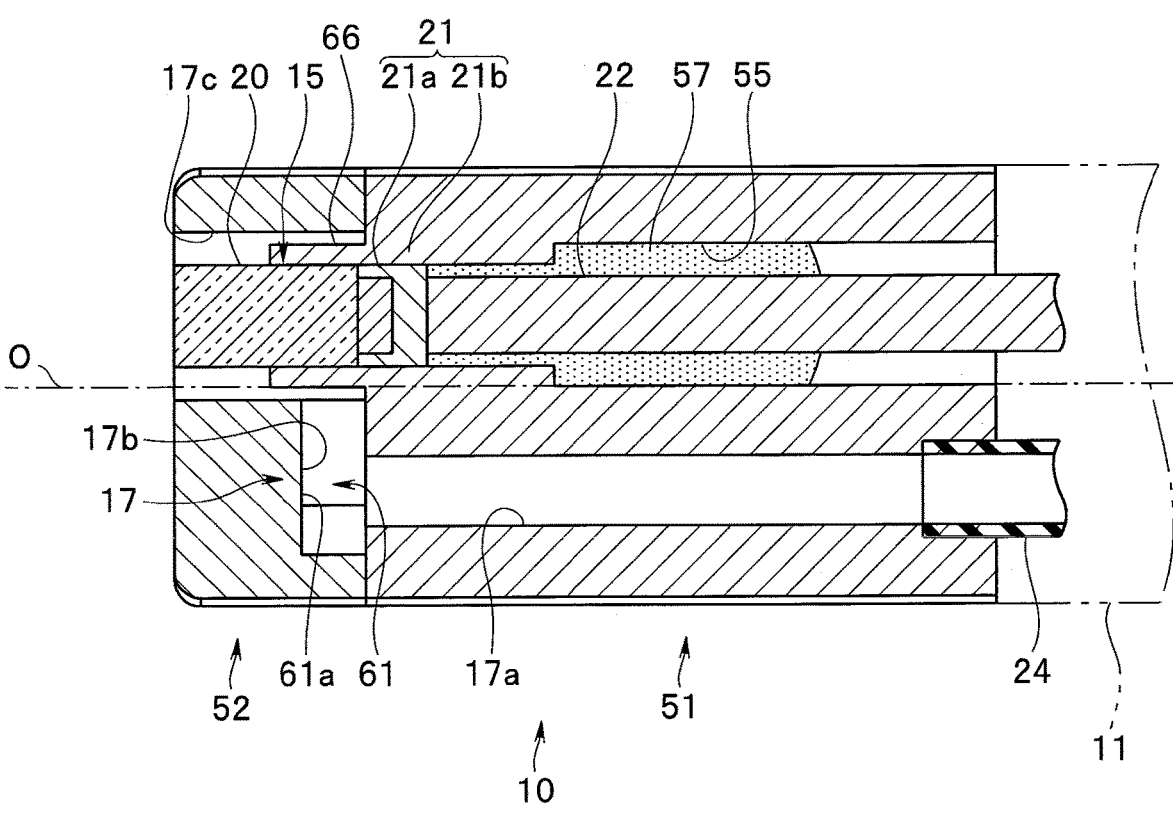
FIG. 19 relates to the modification of the fourth embodiment and is a main part sectional view of the distal end constituting member.

For example, as shown in FIGS. 18 and 19, a length in the longitudinal direction O of the protective frame 66 can also be set to a length surrounding an entire periphery on the proximal end side of the objective optical unit 20.

With the configuration explained above, it is possible to increase the substantial flow path sectional area of the third flow path 17$c$ stepwise in the longitudinal direction O while preventing intrusion of the fluid to the proximal end side beyond the image pickup unit holding hole 55.

Note that the protective frame 66 is not limited to the configuration for surrounding the entire region of the outer periphery of the objective optical unit 20 and may be configured to be disposed along a part of the outer periphery of the objective optical unit 20.

Subsequently, a fifth embodiment of the present disclosure is explained with reference to FIGS. 20 and 21. The present embodiment is different from the first embodiment explained above in that an extension region 67 is provided in the second flow path 17$b$. The distal end constituting portion 10 in the present embodiment includes a gap (a sub-flow path, gap conduit, a fourth flow path 17$d$) for discharging, to the inside of the subject from other than the third flow path 17$c$, a part of the fluid supplied to the second flow path 17$b$. The gap conduit forms a fourth flow path section of the flow path. Further, the distal end constituting portion 10 in the present embodiment includes, for example, a probe insertion hole 68 through which a laser probe for fractured stones (not shown) is inserted. Besides, in the present embodiment, the same components as the components in the first embodiment explained above are denoted by the same reference numerals and signs as the reference numerals and signs in the first embodiment and explanation of the components is omitted as appropriate.

Figure 20:
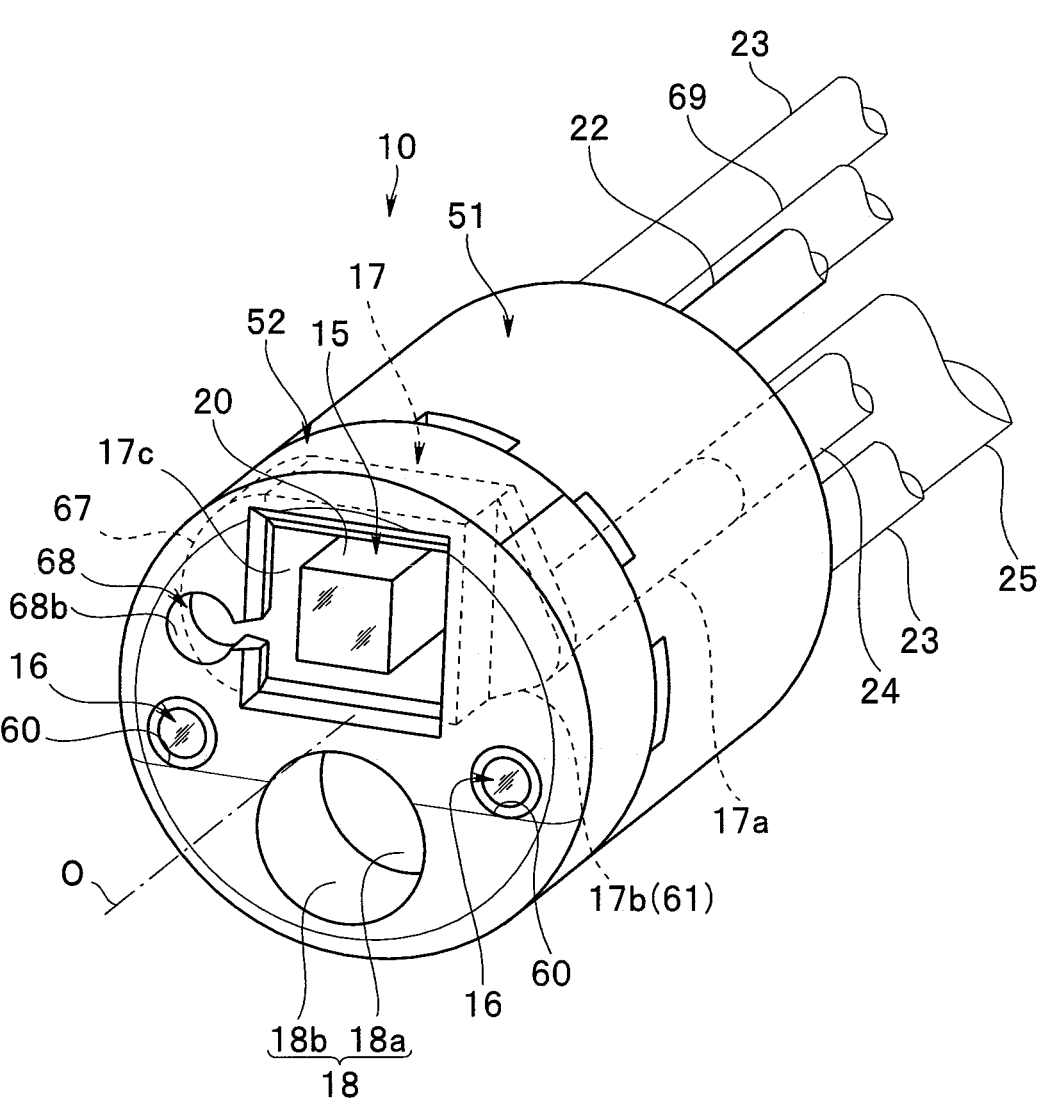
FIG. 20 relates to a fifth embodiment and is a perspective view showing the distal end constituting member from the distal end side.
Figure 21:
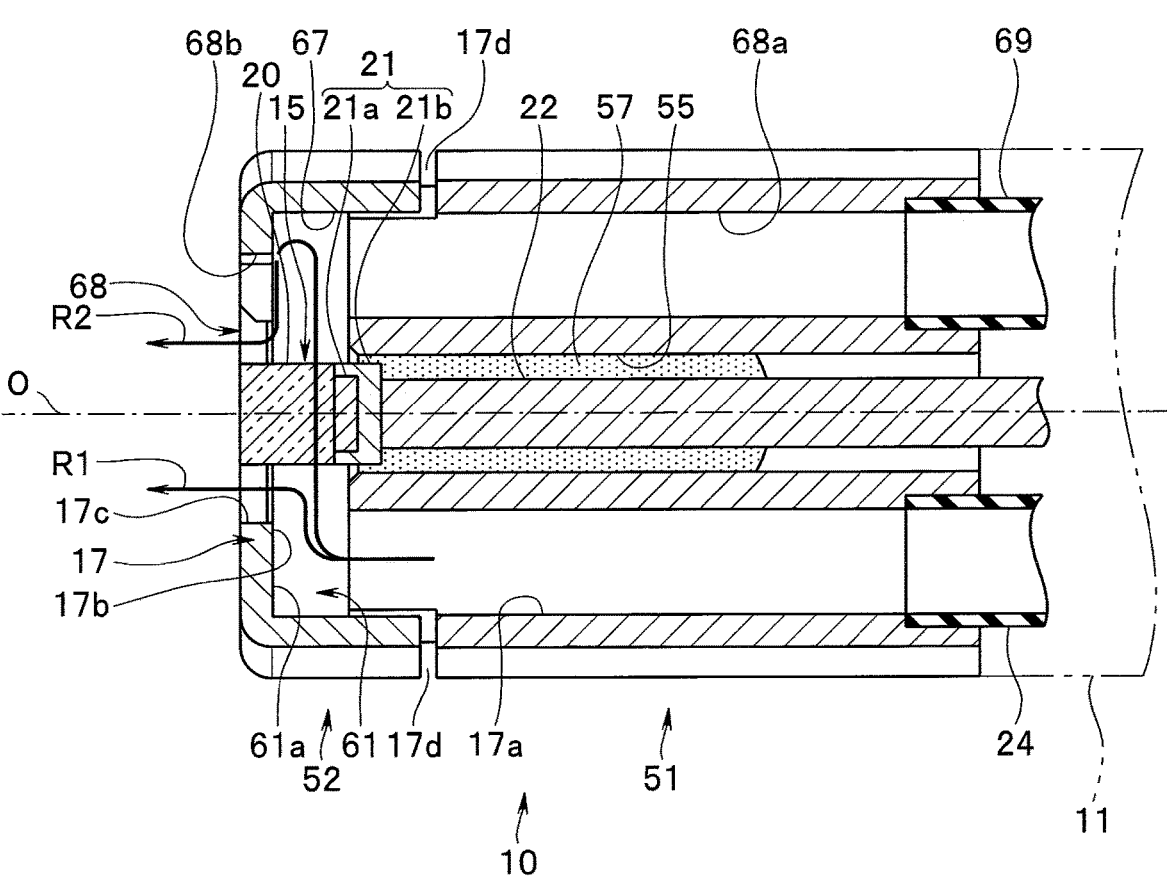
FIG. 21 relates to the fifth embodiment and is a main part sectional view of the distal end constituting member.

As shown in FIG. 20, in the distal end constituting portion 10, the probe insertion hole 68 is provided in a position near the third flow path 17$c$. The probe insertion hole 68 includes a first probe insertion hole 68$a$ and a second probe insertion hole 68$b$.

The first probe insertion hole 68$a$ is configured by, for example, a circular hole that penetrates through the first distal end constituting member 51. The first probe insertion hole 68$a$ extends in the longitudinal direction O of the insertion portion 2. A distal end portion of a probe channel 69 is connected to a proximal end portion of the first probe insertion hole 68$a$.

The second probe insertion hole 68$b$ is configured by, for example, a circular hole that penetrates through the second distal end constituting member 52. The second probe insertion hole 68$b$ extends in the longitudinal direction O of the insertion portion 2. Further, the second probe insertion hole 68$b$ is disposed in a position in line with the first probe insertion hole 68$a$.

For example, the extension region 67 extends the downstream side of the second flow path 17$b$. More specifically, for example, as shown in FIG. 21, the extension region 67 extends, beyond the third flow path 17$c$, the second flow path 17$b$ formed from a position corresponding to the first flow path 17$a$ to a position corresponding to the third flow path 17$c$. Note that, in the present embodiment, the extension region 67 extends the downstream side of the second flow path 17$b$ to a position corresponding to the probe insertion hole 68.

By forming the extension region 67 explained above, a first route (first flow route) R1 and a second route (second flow route) R2 are formed in the second flow path 17$b$. The first route R1 is a route for feeding the fluid to the third flow path 17$c$ not through the extension region 67. The second route R2 is a route for feeding, to the third flow path 17$c$, the fluid after being fed through the extension region 67. The second conduit may include a main region and an extension region 67. The second flow path section located in the main region can be a first flow route and the second flow path section located in the extension region can be a second flow route.

The sub-flow path 17$d$ is formed between the first distal end constituting member 51 and the second distal end constituting member 52. The sub-flow path 17$d$ is a flow path for discharging, from an outer circumferential portion of the distal end constituting portion 10 to the inside of the subject, a part of the fluid flowing in the second flow path 17$b$.

According to the embodiment explained above, the extension region 67 is provided in the second flow path 17$b$ and the first route R1 and the second route R2 are formed as routes for causing the fluid to flow into the third flow path 17$c$ from the second flow path 17$b$. The first route R1 and the second route R2 have different route lengths for the fluid to flow into the third flow path 17$c$. Therefore, the second flow path 17$b$ can differentiate flow velocity of the fluid passed through the first route R1 and flowing into the third flow path 17$c$ and flow velocity of the fluid passed through the second route R2 and flowing into the third flow path 17$c$. It is possible to more effectively clean the distal end face of the observation optical unit 20 by the fluids having the different flow velocities in this way being mixed when being discharged from the third flow path 17$c$. In addition, by mixing the fluids having the different flow velocities, it is possible to efficiently reduce the flow velocity of the fluid discharged from the third flow path 17$c$.

In the present embodiment, a part of the fluid flowing in the second flow path 17$b$ is discharged from the outer circumference of the distal end constituting portion 10 via the sub-flow path 17*d*. Consequently, it is possible to reduce an amount of the fluid discharged from the third flow path 17*c* while maintaining a flow rate of the fluid supplied to the inside of the subject. It is possible to more effectively suppress disturbance of the fluid due to perfusion.

Figure 22:
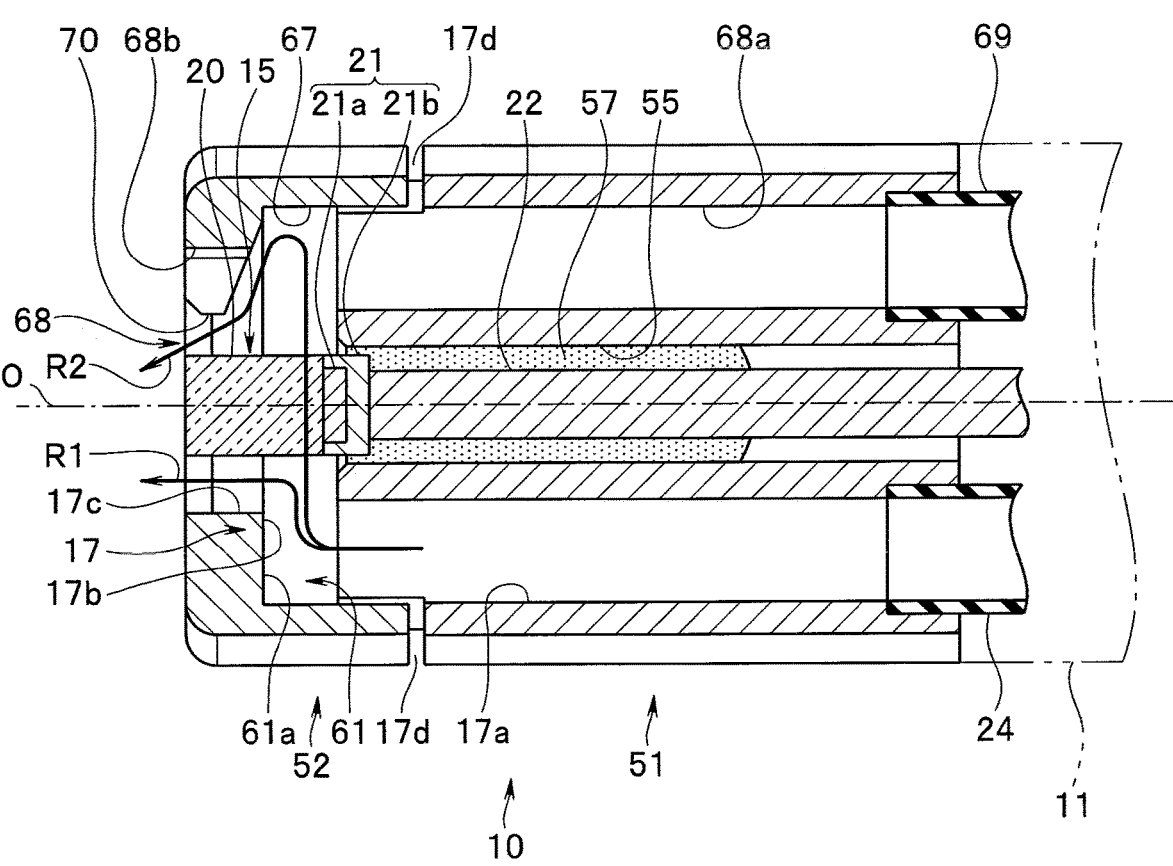
FIG. 22 relates to a modification of the fifth embodiment and is a main part sectional view of the distal end constituting member.

For example, as shown in FIG. 22, a control piece 70 for controlling a direction of the fluid discharged from the third flow path 17*c* can also be provided on an inner wall of a downstream end of the third flow path 17*c*. The control piece 70 is provided, for example, on the second route R2 side. Consequently, the control piece 70 controls the fluid passed through the second route R2 to flow toward the objective optical unit 20. By providing the control piece 70 explained above, for example, it is possible to cause the fluid passed through the second route R2 to collide with the fluid passed through the first route R1. Therefore, it is possible to efficiently mix the fluid passed through the first route R1 and the fluid passed through the second route R2. That is, the control piece 70 has a surface that is a part of the side surface of the opening. The surface redirects the third flow path section toward the objective lens.

Further, in a modification shown in FIG. 22, the upstream side of the third flow path 17*c* is expanded in the longitudinal direction O. Consequently, the upstream side of the third flow path 17*c* functions as, in conjunction with the second flow path 17*b* and the extension region 67, a chamber for rectifying the fluid. Consequently, it is possible to evenly reduce flow velocity of the fluid discharged to the inside of the subject.

Note that the present disclosure is not limited to the respective embodiments explained above, various modifications and changes of the embodiments are possible, and the modifications and the changes are also within a technical scope of the present disclosure.

For example, in the respective embodiments explained above, a configuration in which the entire periphery of the objective optical unit 20 is disposed inside the third flow path 17*c* is explained. However, the present disclosure is not limited to such a configuration. For example, it is also possible to adopt a configuration in which a part of an outer peripheral portion of the objective optical unit 20 is disposed inside the third flow path 17*c*. It goes without saying that configurations of the respective embodiments explained above may be combined as appropriate.

What is claimed is:

1. An insertion instrument, comprising:
an insertion section including a distal end portion, a bending portion, and a flexible tube portion,
wherein, in a longitudinal direction of the insertion section, the bending portion is between the distal end portion and the flexible tube portion,
wherein the flexible tube portion is at a proximal end of the insertion section and the distal end portion is at a distal end of the insertion section,
wherein the distal end portion includes:
an opening in the distal end portion,
an objective lens located in the opening, the objective lens including a front surface and a plurality of side surfaces and having a field of view,
a first conduit extending in the longitudinal direction,
a second conduit connected to the first conduit, the second conduit extending in a direction other than the longitudinal direction,
wherein a space between at least one of the plurality of side surfaces of the objective lens and a side surface of the opening defines a third conduit, the third conduit connected to the second conduit, and wherein the first conduit, the second conduit and the third conduit form a flow path including a first flow path section located in the first conduit, a second flow path section located in the second conduit, and a third flow path section located in the third conduit.

2. The insertion instrument according to claim 1, further comprising:
an image pickup device unit located proximally relative to the objective lens and configured to acquire an optical image via the objective lens; and
a wiring extending from the image pickup device unit to the proximal end of the insertion section.

3. The insertion instrument according to claim 2, wherein at least one of the image pickup device unit and the wiring attaches the objective lens to the distal end portion.

4. The insertion instrument according to claim 3, wherein the distal end portion further comprises an imaging channel, and
wherein at least one of the image pickup device unit and the wiring is bonded to the imaging channel with an adhesive to seal the imaging channel.

5. The insertion instrument according to claim 4, wherein the distal end portion includes a first distal end member and a second distal end member, a proximal end surface of the second distal end member attached to a distal end surface of the first distal end member,
wherein the imaging channel is located in the first distal end member, and
wherein the second conduit is formed in the second distal end member or is formed by the distal end surface of the first distal end member and a recess in the proximal end surface of the second distal end member.

6. The insertion instrument according to claim 5, wherein the distal end portion includes a gap located between the first distal end member and the second distal end member,
wherein the gap defines a gap conduit includes a second opening in an outer surface of the distal end portion and is connected to the second conduit, and
wherein the gap conduit forms a fourth flow path section of the flow path.

7. The insertion instrument according to claim 1, wherein the space defining the third conduit is between an entire circumference of the objective lens and the side surface of the opening.

8. The insertion instrument according to claim 1, wherein the side surface of the opening includes a surface that redirects the third flow path section toward the objective lens.

9. The insertion instrument according to claim 1, wherein a distal end of the second conduit includes a wall section,
wherein a distal end of the first conduit faces the wall section, and
wherein a fluid flowing in the first flow path section contacts the wall section and changes direction to flow in the second flow path section.

10. The insertion instrument according to claim 9, wherein the fluid flowing in the second flow path flows in a direction crossing the longitudinal direction.

11. The insertion instrument according to claim 1, wherein the second conduit has an upstream end and a downstream end,
wherein a cross-sectional area of the second conduit at the upstream end is a first cross-sectional area and a cross-sectional area of the second conduit at the downstream end is a second cross-sectional area, and
wherein the first cross-sectional area is different from the second cross-sectional area.

12. The insertion instrument according to claim 1, wherein a shape of the opening in the distal end surface is a first rectangle having a first area, wherein a shape of a periphery of the objective lens is a second rectangle having a second area, and wherein second area is smaller than the first area.

13. The insertion instrument according to claim 12, wherein a value of a difference between the first area and the second area is a first sectional area, wherein the first conduit has an upstream end and a downstream end, wherein a cross-sectional area of the first conduit at the downstream end is a second sectional area, and wherein the first sectional area is larger than the second sectional area.

14. The insertion instrument according to claim 1, wherein the distal end portion includes a second opening that communicates with a suctioning channel.

15. The insertion instrument according to claim 1, wherein the second conduit includes a main region and an extension region, and wherein the second flow path section located in the main region is a first flow route and the second flow path section located in the extension region is a second flow route.

16. The insertion instrument according to claim 15, wherein the side surface of the opening includes a surface that redirects the third flow path section toward the objective lens.

17. The insertion instrument according to claim 16, wherein the first flow route is connected to the third flow path section.

18. The insertion instrument according to claim 1, wherein the first conduit and the third conduit are longitudinally offset.

19. An endoscope system, comprising the insertion instrument according to claim 1, wherein the insertion instrument is configured to perfuse a fluid between an inside and an outside of a subject.

20. The endoscope system according to claim 19, wherein the distal end portion includes a second opening that communicates with a suctioning channel, and wherein the fluid is supplied from the third conduit and is suctioned through the second opening and the suctioning channel to the outside of the subject.

\* \* \* \* \*